(12) United States Patent
Johnson

(10) Patent No.: US 12,364,587 B2
(45) Date of Patent: Jul. 22, 2025

(54) STORAGE JAR ASSEMBLY FOR A PROSTHETIC HEART VALVE

(71) Applicant: EDWARDS LIFESCIENCES CORPORATION, Irvine, CA (US)

(72) Inventor: Garrett Dallas Johnson, Costa Mesa, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 44 days.

(21) Appl. No.: 18/139,794

(22) Filed: Apr. 26, 2023

(65) Prior Publication Data

US 2024/0074842 A1 Mar. 7, 2024

Related U.S. Application Data

(63) Continuation of application No. PCT/US2021/062690, filed on Dec. 9, 2021.

(60) Provisional application No. 63/199,311, filed on Dec. 18, 2020.

(51) Int. Cl.
| | |
|---|---|
| *A61F 2/24* | (2006.01) |
| *A61B 17/06* | (2006.01) |
| *A61F 2/00* | (2006.01) |
| *B65D 85/30* | (2006.01) |

(52) U.S. Cl.
CPC .................. *A61F 2/0095* (2013.01)

(58) Field of Classification Search
CPC ...... B65D 81/02; A61F 2/0095; A61F 2/2418; A61B 50/30
USPC ........... 206/363, 438; 215/228, 386; 623/2.1
See application file for complete search history.

(56) References Cited

U.S. PATENT DOCUMENTS

| | | | |
|---|---|---|---|
| 3,409,013 A | 11/1968 | Berry | |
| 3,472,230 A | 10/1969 | Fogarty | |
| 3,548,417 A | 12/1970 | Kischer et al. | |
| 3,587,115 A | 6/1971 | Shiley | |
| 3,657,744 A | 4/1972 | Ersek | |
| 3,671,979 A | 6/1972 | Moulopoulos | |
| 3,714,671 A | 2/1973 | Edwards et al. | |
| 3,739,402 A | 6/1973 | Cooley et al. | |

(Continued)

FOREIGN PATENT DOCUMENTS

| | | |
|---|---|---|
| CA | 2304325 C | 5/2008 |
| DE | 2246526 A1 | 3/1973 |

(Continued)

OTHER PUBLICATIONS

Andersen, et al., "Transluminal implantation of artificial heart valves. Description of a new expandable aortic valve and initial results with implantation by catheter technique in closed chest pigs." European Heart Journal (1992), 13, 704-708.

(Continued)

*Primary Examiner* — Luan K Bui
(74) *Attorney, Agent, or Firm* — Thomas C. Richardson

(57) ABSTRACT

A storage jar assembly for use with a prosthetic heart valve is disclosed in several embodiments. As one example, a storage jar assembly can include a jar having an open end and configured to receive a prosthetic heart valve. The embodiment also includes a lid configured to cover the open end of the jar. The lid can include a plurality of valve attachment features configured to be releasably attached to corresponding features of the prosthetic heart valve.

19 Claims, 14 Drawing Sheets

(56) References Cited

U.S. PATENT DOCUMENTS

| | | |
|---|---|---|
| 3,755,823 A | 9/1973 | Hancock |
| 4,035,849 A | 7/1977 | Angell et al. |
| 4,056,854 A | 11/1977 | Boretos et al. |
| 4,079,468 A | 3/1978 | Liotta et al. |
| 4,106,129 A | 8/1978 | Carpentier et al. |
| 4,204,283 A | 5/1980 | Bellhouse et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,340,977 A | 7/1982 | Brownlee et al. |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,477,930 A | 10/1984 | Totten et al. |
| 4,490,859 A | 1/1985 | Black et al. |
| 4,535,483 A | 8/1985 | Klawitter et al. |
| 4,553,545 A | 11/1985 | Maass et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,829,990 A | 5/1989 | Thuroff et al. |
| 4,851,001 A | 7/1989 | Taheri |
| 4,856,516 A | 8/1989 | Hillstead |
| 4,865,600 A | 9/1989 | Carpentier et al. |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,108,370 A | 4/1992 | Walinsky |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,232,446 A | 8/1993 | Arney |
| 5,266,073 A | 11/1993 | Wall |
| 5,282,847 A | 2/1994 | Trescony et al. |
| 5,295,958 A | 3/1994 | Shturman |
| 5,326,371 A | 7/1994 | Love et al. |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,522 A | 5/1995 | Trott |
| 5,411,552 A | 5/1995 | Andersen et al. |
| 5,415,667 A | 5/1995 | Frater |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,571,175 A | 11/1996 | Vanney et al. |
| 5,591,185 A | 1/1997 | Kilmer et al. |
| 5,599,305 A | 2/1997 | Hermann et al. |
| 5,607,464 A | 3/1997 | Trescony et al. |
| 5,609,626 A | 3/1997 | Quijano et al. |
| 5,639,274 A | 6/1997 | Fischell et al. |
| 5,665,115 A | 9/1997 | Cragg |
| 5,697,382 A | 12/1997 | Love et al. |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,906,619 A | 5/1999 | Olson et al. |
| 5,925,063 A | 7/1999 | Khosravi |
| 5,957,949 A | 9/1999 | Leonhardt et al. |
| 5,968,068 A | 10/1999 | Dehdashtian et al. |
| 6,027,525 A | 2/2000 | Suh et al. |
| 6,042,607 A | 3/2000 | Williamson et al. |
| 6,086,612 A | 7/2000 | Jansen |
| 6,113,631 A | 9/2000 | Jansen |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,040 B1 | 6/2001 | Inderbitzen et al. |
| 6,245,102 B1 | 6/2001 | Jayaraman |
| 6,251,093 B1 | 6/2001 | Valley et al. |
| 6,287,339 B1 | 9/2001 | Vazquez et al. |
| 6,299,637 B1 | 10/2001 | Shaolian et al. |
| 6,302,906 B1 | 10/2001 | Goicoechea et al. |
| 6,306,141 B1 | 10/2001 | Jervis |
| 6,312,465 B1 | 11/2001 | Griffin et al. |
| 6,350,277 B1 | 2/2002 | Kocur |
| 6,358,277 B1 | 3/2002 | Duran |
| 6,379,372 B1 | 4/2002 | Dehdashtian et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,527,800 B1 | 3/2003 | McGuckin et al. |
| 6,527,979 B2 | 3/2003 | Constantz et al. |
| 6,540,782 B1 | 4/2003 | Snyders |
| 6,569,196 B1 | 5/2003 | Vesely |
| 6,575,959 B1 | 6/2003 | Sarge et al. |
| 6,582,462 B1 | 6/2003 | Andersen et al. |
| 6,605,112 B1 | 8/2003 | Moll et al. |
| 6,610,088 B1 | 8/2003 | Gabbay |
| 6,629,534 B1 | 10/2003 | St. Goar et al. |
| 6,676,698 B2 | 1/2004 | McGuckin et al. |
| 6,695,878 B2 | 2/2004 | McGuckin et al. |
| 6,712,836 B1 | 3/2004 | Berg et al. |
| 6,716,207 B2 | 4/2004 | Farnholtz |
| 6,729,356 B1 | 5/2004 | Baker et al. |
| 6,730,118 B2 | 5/2004 | Spenser et al. |
| 6,733,525 B2 | 5/2004 | Yang et al. |
| 6,746,422 B1 | 6/2004 | Noriega et al. |
| 6,749,560 B1 | 6/2004 | Konstorum et al. |
| 6,767,362 B2 | 7/2004 | Schreck |
| 6,780,200 B2 | 8/2004 | Jansen |
| 6,790,229 B1 | 9/2004 | Berreklouw |

(56) References Cited

U.S. PATENT DOCUMENTS

| | | |
|---|---|---|
| 6,790,230 B2 | 9/2004 | Beyersdorf et al. |
| 6,830,584 B1 | 12/2004 | Seguin |
| 6,875,231 B2 | 4/2005 | Anduiza et al. |
| 6,893,460 B2 | 5/2005 | Spenser et al. |
| 6,908,481 B2 | 6/2005 | Cribier |
| 6,974,476 B2 | 12/2005 | McGuckin et al. |
| 7,018,406 B2 | 3/2006 | Seguin et al. |
| 7,186,265 B2 | 3/2007 | Sharkawy et al. |
| 7,192,440 B2 | 3/2007 | Andreas et al. |
| 7,198,646 B2 | 4/2007 | Figulla et al. |
| 7,201,772 B2 | 4/2007 | Schwammenthal et al. |
| 7,276,078 B2 | 10/2007 | Spenser et al. |
| 7,276,084 B2 | 10/2007 | Yang et al. |
| 7,318,278 B2 | 1/2008 | Zhang et al. |
| 7,374,571 B2 | 5/2008 | Pease et al. |
| 7,381,210 B2 | 6/2008 | Zarbatany et al. |
| 7,381,219 B2 | 6/2008 | Salahieh et al. |
| 7,389,874 B2 * | 6/2008 | Quest ............ A61F 2/2427 206/363 |
| 7,393,360 B2 | 7/2008 | Spenser et al. |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,510,575 B2 | 3/2009 | Spenser et al. |
| 7,524,330 B2 | 4/2009 | Berreklouw |
| 7,530,253 B2 | 5/2009 | Spenser et al. |
| 7,553,324 B2 | 6/2009 | Andreas et al. |
| 7,579,381 B2 | 8/2009 | Dove |
| 7,585,321 B2 | 9/2009 | Cribier |
| 7,618,446 B2 | 11/2009 | Andersen et al. |
| 7,621,948 B2 | 11/2009 | Herrmann et al. |
| 7,704,222 B2 | 4/2010 | Wilk et al. |
| 7,736,327 B2 | 6/2010 | Wilk et al. |
| 7,748,389 B2 | 7/2010 | Salahieh et al. |
| 7,753,949 B2 | 7/2010 | Lamphere et al. |
| 7,806,919 B2 | 10/2010 | Bloom et al. |
| 7,824,443 B2 | 11/2010 | Salahieh et al. |
| 7,837,727 B2 | 11/2010 | Goetz et al. |
| 7,892,281 B2 | 2/2011 | Seguin et al. |
| 7,914,569 B2 | 3/2011 | Nguyen et al. |
| 7,914,575 B2 | 3/2011 | Guyenot et al. |
| 7,959,672 B2 | 6/2011 | Salahieh et al. |
| 7,972,378 B2 | 7/2011 | Tabor et al. |
| 7,981,151 B2 | 7/2011 | Rowe |
| 7,993,392 B2 | 8/2011 | Righini et al. |
| 7,993,394 B2 | 8/2011 | Hariton et al. |
| 8,007,992 B2 | 8/2011 | Tian et al. |
| 8,016,877 B2 | 9/2011 | Seguin et al. |
| 8,029,556 B2 | 10/2011 | Rowe |
| 8,052,750 B2 | 11/2011 | Tuval et al. |
| 8,070,800 B2 | 12/2011 | Lock et al. |
| 8,070,802 B2 | 12/2011 | Lamphere et al. |
| 8,075,615 B2 | 12/2011 | Eberhardt et al. |
| 8,080,054 B2 | 12/2011 | Rowe |
| 8,092,520 B2 | 1/2012 | Quadri |
| 8,092,521 B2 | 1/2012 | Figulla et al. |
| 8,109,996 B2 | 2/2012 | Stacchino et al. |
| 8,118,866 B2 | 2/2012 | Herrmann et al. |
| 8,136,218 B2 | 3/2012 | Millwee et al. |
| 8,137,398 B2 | 3/2012 | Tuval et al. |
| 8,157,852 B2 | 4/2012 | Bloom et al. |
| 8,167,932 B2 | 5/2012 | Bourang et al. |
| 8,167,934 B2 | 5/2012 | Styrc et al. |
| 8,182,530 B2 | 5/2012 | Huber |
| 8,206,437 B2 | 6/2012 | Bonhoeffer et al. |
| 8,216,174 B2 | 7/2012 | Wilk et al. |
| 8,216,301 B2 | 7/2012 | Bonhoeffer et al. |
| 8,219,229 B2 | 7/2012 | Cao et al. |
| 8,220,121 B2 | 7/2012 | Hendriksen et al. |
| 8,236,045 B2 | 8/2012 | Benichou et al. |
| 8,246,675 B2 | 8/2012 | Zegdi |
| 8,246,678 B2 | 8/2012 | Salahieh et al. |
| 8,252,051 B2 | 8/2012 | Chau et al. |
| 8,252,052 B2 | 8/2012 | Salahieh et al. |
| 8,287,584 B2 | 10/2012 | Salahieh et al. |
| 8,313,525 B2 | 11/2012 | Tuval et al. |
| 8,317,858 B2 | 11/2012 | Straubinger et al. |
| 8,323,335 B2 | 12/2012 | Rowe et al. |
| 8,337,541 B2 | 12/2012 | Quadri et al. |
| 8,353,953 B2 | 1/2013 | Giannetti et al. |
| 8,398,704 B2 | 3/2013 | Straubinger et al. |
| 8,403,983 B2 | 3/2013 | Quadri et al. |
| 8,414,644 B2 | 4/2013 | Quadri et al. |
| 8,414,645 B2 | 4/2013 | Dwork et al. |
| 8,416,643 B2 | 4/2013 | Magee |
| 8,444,689 B2 | 5/2013 | Zhang |
| 8,449,599 B2 | 5/2013 | Chau et al. |
| 8,454,685 B2 | 6/2013 | Hariton et al. |
| 8,460,368 B2 | 6/2013 | Taylor et al. |
| 8,460,370 B2 | 6/2013 | Zakay et al. |
| 8,470,023 B2 | 6/2013 | Eidenschink et al. |
| 8,470,028 B2 | 6/2013 | Thornton et al. |
| 8,475,521 B2 | 7/2013 | Suri et al. |
| 8,475,523 B2 | 7/2013 | Duffy |
| 8,479,380 B2 | 7/2013 | Malewicz et al. |
| 8,491,650 B2 | 7/2013 | Wiemeyer et al. |
| 8,500,733 B2 | 8/2013 | Watson |
| 8,500,798 B2 | 8/2013 | Rowe et al. |
| 8,511,244 B2 | 8/2013 | Holecek et al. |
| 8,512,401 B2 | 8/2013 | Murray et al. |
| 8,518,096 B2 | 8/2013 | Nelson |
| 8,518,106 B2 | 8/2013 | Duffy et al. |
| 8,562,663 B2 | 10/2013 | Mearns et al. |
| 8,579,963 B2 | 11/2013 | Tabor |
| 8,579,964 B2 | 11/2013 | Lane et al. |
| 8,591,570 B2 | 11/2013 | Revuelta et al. |
| 8,617,236 B2 | 12/2013 | Paul et al. |
| 8,640,521 B2 | 2/2014 | Righini et al. |
| 8,647,381 B2 | 2/2014 | Essinger et al. |
| 8,652,145 B2 | 2/2014 | Maimon et al. |
| 8,652,201 B2 | 2/2014 | Oberti et al. |
| 8,652,202 B2 | 2/2014 | Alon et al. |
| 8,652,203 B2 | 2/2014 | Quadri et al. |
| 8,668,733 B2 | 3/2014 | Haug et al. |
| 8,679,174 B2 | 3/2014 | Ottma et al. |
| 8,679,404 B2 | 3/2014 | Liburd et al. |
| 8,685,086 B2 | 4/2014 | Navia et al. |
| 8,721,708 B2 | 5/2014 | Sèguin et al. |
| 8,721,714 B2 | 5/2014 | Kelley |
| 8,728,154 B2 | 5/2014 | Alkhatib |
| 8,728,155 B2 | 5/2014 | Montorfano et al. |
| 8,740,974 B2 | 6/2014 | Lambrecht et al. |
| 8,740,976 B2 | 6/2014 | Tran et al. |
| 8,747,458 B2 | 6/2014 | Tuval et al. |
| 8,747,459 B2 | 6/2014 | Nguyen et al. |
| 8,758,432 B2 | 6/2014 | Solem |
| 8,764,818 B2 | 7/2014 | Gregg |
| 8,771,344 B2 | 7/2014 | Tran et al. |
| 8,778,020 B2 | 7/2014 | Gregg et al. |
| 8,784,337 B2 | 7/2014 | Voeller et al. |
| 8,784,478 B2 | 7/2014 | Tuval et al. |
| 8,784,481 B2 | 7/2014 | Alkhatib et al. |
| 8,790,387 B2 | 7/2014 | Nguyen et al. |
| 8,795,357 B2 | 8/2014 | Yohanan et al. |
| 8,808,356 B2 | 8/2014 | Braido et al. |
| 8,828,078 B2 | 9/2014 | Salahieh et al. |
| 8,828,079 B2 | 9/2014 | Thielen et al. |
| 8,834,564 B2 | 9/2014 | Tuval et al. |
| 8,839,957 B2 * | 9/2014 | Murad ............ A61F 2/0095 206/363 |
| 8,858,620 B2 | 10/2014 | Salahieh et al. |
| 8,870,948 B1 | 10/2014 | Erzberger et al. |
| 8,870,950 B2 | 10/2014 | Hacohen |
| 8,876,893 B2 | 11/2014 | Dwork et al. |
| 8,911,455 B2 | 12/2014 | Quadri et al. |
| 8,926,693 B2 | 1/2015 | Duffy et al. |
| 8,926,694 B2 | 1/2015 | Costello |
| 8,939,960 B2 | 1/2015 | Rosenman et al. |
| 8,945,209 B2 | 2/2015 | Bonyuet et al. |
| 8,961,593 B2 | 2/2015 | Bonhoeffer et al. |
| 8,961,595 B2 | 2/2015 | Alkhatib |
| 8,974,524 B2 | 3/2015 | Yeung et al. |
| 8,979,922 B2 | 3/2015 | Jayasinghe et al. |

(56) References Cited

U.S. PATENT DOCUMENTS

| | | |
|---|---|---|
| 8,986,375 B2 | 3/2015 | Garde et al. |
| 8,998,980 B2 | 4/2015 | Shipley et al. |
| 9,005,273 B2 | 4/2015 | Salahieh et al. |
| 9,011,521 B2 | 4/2015 | Haug et al. |
| 9,011,523 B2 | 4/2015 | Seguin |
| 9,011,524 B2 | 4/2015 | Eberhardt |
| 9,028,545 B2 | 5/2015 | Taylor |
| 9,034,032 B2 | 5/2015 | McLean et al. |
| 9,055,937 B2 | 6/2015 | Rowe et al. |
| 9,066,801 B2 | 6/2015 | Kovalsky et al. |
| 9,078,749 B2 | 7/2015 | Lutter et al. |
| 9,078,751 B2 | 7/2015 | Naor |
| 9,114,010 B2 * | 8/2015 | Gaschino .............. A61F 2/2427 |
| 9,125,738 B2 | 9/2015 | Figulla et al. |
| 9,173,737 B2 | 11/2015 | Hill et al. |
| 9,180,004 B2 | 11/2015 | Alkhatib |
| 9,186,249 B2 | 11/2015 | Rolando et al. |
| 9,277,990 B2 | 3/2016 | Klima et al. |
| 9,277,993 B2 | 3/2016 | Gamarra et al. |
| 9,289,291 B2 | 3/2016 | Gorman et al. |
| 9,295,551 B2 | 3/2016 | Straubinger et al. |
| 9,445,897 B2 | 9/2016 | Bishop et al. |
| 9,456,877 B2 | 10/2016 | Weitzner et al. |
| 9,681,968 B2 | 6/2017 | Goetz et al. |
| 9,687,345 B2 | 6/2017 | Rabito et al. |
| 9,700,329 B2 | 7/2017 | Metzger et al. |
| 9,700,411 B2 | 7/2017 | Klima et al. |
| 9,724,083 B2 | 8/2017 | Quadri et al. |
| 9,730,790 B2 | 8/2017 | Quadri et al. |
| 9,730,791 B2 | 8/2017 | Ratz et al. |
| 9,795,479 B2 | 10/2017 | Lim et al. |
| 9,833,313 B2 | 12/2017 | Board et al. |
| 9,861,473 B2 | 1/2018 | Lafontaine |
| 9,861,476 B2 | 1/2018 | Salahieh et al. |
| 9,861,477 B2 | 1/2018 | Backus et al. |
| 9,867,698 B2 | 1/2018 | Kovalsky et al. |
| 9,877,830 B2 | 1/2018 | Lim et al. |
| 9,889,029 B2 | 2/2018 | Li et al. |
| 9,895,225 B2 | 2/2018 | Rolando et al. |
| 9,925,045 B2 | 3/2018 | Creaven et al. |
| 10,004,599 B2 | 6/2018 | Rabito et al. |
| 10,117,744 B2 | 11/2018 | Ratz et al. |
| 10,179,044 B2 | 1/2019 | Ratz et al. |
| 10,219,897 B2 | 3/2019 | Essinger et al. |
| 10,350,065 B2 | 7/2019 | Quadri |
| 10,350,066 B2 | 7/2019 | Cooper et al. |
| 10,376,363 B2 | 8/2019 | Quadri et al. |
| 10,555,809 B2 | 2/2020 | Hastings et al. |
| 10,575,951 B2 | 3/2020 | Johnson et al. |
| 10,583,000 B2 | 3/2020 | Ratz et al. |
| 10,639,146 B2 | 5/2020 | Quadri et al. |
| 10,695,177 B2 | 6/2020 | Hariton et al. |
| 10,758,344 B2 | 9/2020 | Hariton et al. |
| 11,406,499 B2 | 8/2022 | Zhang et al. |
| 11,452,598 B2 | 9/2022 | Essinger et al. |
| 11,672,658 B2 | 6/2023 | Hariton et al. |
| 11,701,225 B2 | 7/2023 | Hammer et al. |
| 11,903,829 B1 | 2/2024 | Ma et al. |
| 2001/0021872 A1 | 9/2001 | Bailey et al. |
| 2002/0032481 A1 | 3/2002 | Gabbay |
| 2002/0045929 A1 | 4/2002 | Diaz |
| 2002/0052644 A1 | 5/2002 | Shaolian et al. |
| 2002/0173842 A1 | 11/2002 | Buchanan |
| 2003/0050694 A1 | 3/2003 | Yang et al. |
| 2003/0100939 A1 | 5/2003 | Yodfat et al. |
| 2003/0105517 A1 | 6/2003 | White et al. |
| 2003/0120333 A1 | 6/2003 | Ouriel et al. |
| 2003/0130729 A1 | 7/2003 | Paniagua et al. |
| 2003/0158597 A1 | 8/2003 | Quiachon et al. |
| 2003/0176914 A1 | 9/2003 | Rabkin et al. |
| 2003/0199971 A1 | 10/2003 | Tower et al. |
| 2003/0212454 A1 | 11/2003 | Scott et al. |
| 2003/0220683 A1 | 11/2003 | Minasian et al. |
| 2004/0039436 A1 | 2/2004 | Spenser et al. |
| 2004/0092858 A1 | 5/2004 | Wilson et al. |
| 2004/0117009 A1 | 6/2004 | Cali et al. |
| 2004/0133263 A1 | 7/2004 | Dusbabek et al. |
| 2004/0133273 A1 | 7/2004 | Cox |
| 2004/0186563 A1 | 9/2004 | Lobbi |
| 2004/0186565 A1 | 9/2004 | Schreck |
| 2004/0210307 A1 | 10/2004 | Khairkhahan |
| 2004/0215325 A1 | 10/2004 | Penn et al. |
| 2004/0225353 A1 | 11/2004 | McGuckin et al. |
| 2004/0236411 A1 | 11/2004 | Sarac et al. |
| 2004/0260389 A1 | 12/2004 | Case et al. |
| 2005/0033398 A1 | 2/2005 | Seguin |
| 2005/0075727 A1 | 4/2005 | Wheatley |
| 2005/0090887 A1 | 4/2005 | Pryor |
| 2005/0096738 A1 | 5/2005 | Cali et al. |
| 2005/0107872 A1 | 5/2005 | Mensah et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137691 A1 | 6/2005 | Salahieh et al. |
| 2005/0137698 A1 | 6/2005 | Salahieh et al. |
| 2005/0159811 A1 | 7/2005 | Lane |
| 2005/0182486 A1 | 8/2005 | Gabbay |
| 2005/0203614 A1 | 9/2005 | Forster et al. |
| 2005/0203617 A1 | 9/2005 | Forster et al. |
| 2005/0216079 A1 | 9/2005 | MaCoviak |
| 2005/0234546 A1 | 10/2005 | Nugent et al. |
| 2005/0288766 A1 | 12/2005 | Plain et al. |
| 2006/0020327 A1 | 1/2006 | Lashinski et al. |
| 2006/0025857 A1 | 2/2006 | Bergheim et al. |
| 2006/0058872 A1 | 3/2006 | Salahieh et al. |
| 2006/0095115 A1 | 5/2006 | Bladillah et al. |
| 2006/0142837 A1 | 6/2006 | Haverkost et al. |
| 2006/0149350 A1 | 7/2006 | Patel et al. |
| 2006/0161249 A1 | 7/2006 | Realyvasquez et al. |
| 2006/0173537 A1 | 8/2006 | Yang et al. |
| 2006/0195134 A1 | 8/2006 | Crittenden |
| 2006/0195183 A1 | 8/2006 | Navia et al. |
| 2006/0212110 A1 | 9/2006 | Osborne et al. |
| 2006/0229719 A1 | 10/2006 | Marquez et al. |
| 2006/0241745 A1 | 10/2006 | Solem |
| 2006/0259135 A1 | 11/2006 | Navia et al. |
| 2006/0259137 A1 | 11/2006 | Artof et al. |
| 2006/0276874 A1 | 12/2006 | Wilson et al. |
| 2006/0293745 A1 | 12/2006 | Carpentier et al. |
| 2007/0005131 A1 | 1/2007 | Taylor |
| 2007/0010877 A1 | 1/2007 | Salahieh et al. |
| 2007/0027534 A1 | 2/2007 | Bergheim et al. |
| 2007/0043435 A1 | 2/2007 | Seguin et al. |
| 2007/0050021 A1 | 3/2007 | Johnson |
| 2007/0066863 A1 | 3/2007 | Rafiee et al. |
| 2007/0088431 A1 | 4/2007 | Bourang et al. |
| 2007/0100432 A1 | 5/2007 | Case et al. |
| 2007/0100439 A1 | 5/2007 | Cangialosi et al. |
| 2007/0112422 A1 | 5/2007 | Dehdashtian |
| 2007/0129794 A1 | 6/2007 | Realyvasquez |
| 2007/0142906 A1 | 6/2007 | Figulla et al. |
| 2007/0156224 A1 | 7/2007 | Cioanta et al. |
| 2007/0203503 A1 | 8/2007 | Salahieh et al. |
| 2007/0203575 A1 | 8/2007 | Forster et al. |
| 2007/0213813 A1 | 9/2007 | Von Segesser et al. |
| 2007/0255394 A1 | 11/2007 | Ryan |
| 2007/0270943 A1 | 11/2007 | Solem et al. |
| 2008/0021546 A1 | 1/2008 | Patz et al. |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0082164 A1 | 4/2008 | Friedman |
| 2008/0082165 A1 | 4/2008 | Wilson et al. |
| 2008/0082166 A1 | 4/2008 | Styrc et al. |
| 2008/0097581 A1 | 4/2008 | Shanley |
| 2008/0114442 A1 | 5/2008 | Mitchell et al. |
| 2008/0125853 A1 | 5/2008 | Bailey et al. |
| 2008/0147179 A1 | 6/2008 | Cai et al. |
| 2008/0147183 A1 | 6/2008 | Styrc |

(56) References Cited

U.S. PATENT DOCUMENTS

| | | |
|---|---|---|
| 2008/0154355 A1 | 6/2008 | Benichou et al. |
| 2008/0161910 A1 | 7/2008 | Revuelta et al. |
| 2008/0177381 A1 | 7/2008 | Navia et al. |
| 2008/0183273 A1 | 7/2008 | Mesana et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0228254 A1 | 9/2008 | Ryan |
| 2008/0255660 A1 | 10/2008 | Guyenot et al. |
| 2008/0255661 A1 | 10/2008 | Straubinger et al. |
| 2008/0281411 A1 | 11/2008 | Berreklouw |
| 2009/0005863 A1 | 1/2009 | Goetz et al. |
| 2009/0054968 A1 | 2/2009 | Bonhoeffer et al. |
| 2009/0054974 A1 | 2/2009 | McGuckin et al. |
| 2009/0076598 A1 | 3/2009 | Salahieh et al. |
| 2009/0112309 A1 | 4/2009 | Jaramillo et al. |
| 2009/0138079 A1 | 5/2009 | Tuval et al. |
| 2009/0157175 A1 | 6/2009 | Benichou |
| 2009/0164005 A1 | 6/2009 | Dove et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0182413 A1 | 7/2009 | Burkart et al. |
| 2009/0188964 A1 | 7/2009 | Orlov |
| 2009/0216310 A1 | 8/2009 | Straubinger et al. |
| 2009/0216313 A1 | 8/2009 | Straubinger et al. |
| 2009/0216322 A1 | 8/2009 | Le et al. |
| 2009/0222076 A1 | 9/2009 | Figulla et al. |
| 2009/0234443 A1 | 9/2009 | Ottma et al. |
| 2009/0240320 A1 | 9/2009 | Tuval et al. |
| 2009/0270972 A1 | 10/2009 | Lane |
| 2009/0276027 A1 | 11/2009 | Glynn |
| 2009/0276040 A1 | 11/2009 | Rowe et al. |
| 2009/0281618 A1 | 11/2009 | Hill et al. |
| 2009/0281619 A1 | 11/2009 | Le et al. |
| 2009/0287296 A1 | 11/2009 | Manasse |
| 2009/0287299 A1 | 11/2009 | Tabor et al. |
| 2009/0292350 A1 | 11/2009 | Eberhardt et al. |
| 2009/0306768 A1 | 12/2009 | Quadri |
| 2009/0319037 A1 | 12/2009 | Rowe et al. |
| 2010/0016958 A1 | 1/2010 | St. Goar et al. |
| 2010/0049313 A1 | 2/2010 | Alon et al. |
| 2010/0069852 A1 | 3/2010 | Kelley |
| 2010/0114305 A1 | 5/2010 | Kang et al. |
| 2010/0131054 A1 | 5/2010 | Tuval et al. |
| 2010/0137979 A1 | 6/2010 | Tuval et al. |
| 2010/0174362 A1 | 7/2010 | Straubinger et al. |
| 2010/0191326 A1 | 7/2010 | Alkhatib |
| 2010/0204781 A1 | 8/2010 | Alkhatib |
| 2010/0217382 A1 | 8/2010 | Chau et al. |
| 2010/0249894 A1 | 9/2010 | Oba et al. |
| 2010/0249911 A1 | 9/2010 | Alkhatib |
| 2010/0256723 A1 | 10/2010 | Murray |
| 2010/0262231 A1 | 10/2010 | Tuval et al. |
| 2010/0305685 A1 | 12/2010 | Millwee et al. |
| 2010/0312333 A1 | 12/2010 | Navia et al. |
| 2011/0015616 A1 | 1/2011 | Straubinger et al. |
| 2011/0015729 A1 | 1/2011 | Jimenez et al. |
| 2011/0137397 A1 | 6/2011 | Chau et al. |
| 2011/0178597 A9 | 7/2011 | Navia et al. |
| 2011/0208290 A1 | 8/2011 | Straubinger et al. |
| 2011/0208297 A1 | 8/2011 | Tuval et al. |
| 2011/0208298 A1 | 8/2011 | Tuval et al. |
| 2011/0224785 A1 | 9/2011 | Hacohen |
| 2011/0238159 A1 | 9/2011 | Guyenot et al. |
| 2011/0264196 A1 | 10/2011 | Savage et al. |
| 2011/0264198 A1 | 10/2011 | Murray et al. |
| 2011/0288634 A1 | 11/2011 | Tuval et al. |
| 2011/0313515 A1 | 12/2011 | Quadri et al. |
| 2011/0319989 A1 | 12/2011 | Lane et al. |
| 2012/0022639 A1 | 1/2012 | Hacohen et al. |
| 2012/0035722 A1 | 2/2012 | Tuval |
| 2012/0041550 A1 | 2/2012 | Salahieh et al. |
| 2012/0046741 A1 | 2/2012 | Tuval et al. |
| 2012/0046742 A1 | 2/2012 | Tuval et al. |
| 2012/0078360 A1 | 3/2012 | Rafiee |
| 2012/0101570 A1 | 4/2012 | Tuval et al. |
| 2012/0101571 A1 | 4/2012 | Thambar et al. |
| 2012/0101572 A1 | 4/2012 | Kovalsky et al. |
| 2012/0123529 A1 | 5/2012 | Levi et al. |
| 2012/0185039 A1 | 7/2012 | Tuval et al. |
| 2012/0197386 A1 | 8/2012 | Von Segesser et al. |
| 2012/0209374 A1 | 8/2012 | Bonhoeffer et al. |
| 2012/0215303 A1 | 8/2012 | Quadri et al. |
| 2012/0271398 A1 | 10/2012 | Essinger et al. |
| 2012/0283823 A1 | 11/2012 | Bonhoeffer et al. |
| 2012/0290062 A1 | 11/2012 | McNamara et al. |
| 2012/0290079 A1* | 11/2012 | Murad .................. A61F 2/2412 623/2.17 |
| 2012/0296418 A1 | 11/2012 | Bonyuet et al. |
| 2012/0310328 A1 | 12/2012 | Olson et al. |
| 2012/0310336 A1 | 12/2012 | Figulla et al. |
| 2013/0006294 A1 | 1/2013 | Kashkarov et al. |
| 2013/0035759 A1 | 2/2013 | Gross et al. |
| 2013/0073035 A1 | 3/2013 | Tuval et al. |
| 2013/0079869 A1 | 3/2013 | Straubinger et al. |
| 2013/0190861 A1 | 7/2013 | Chau et al. |
| 2013/0190862 A1 | 7/2013 | Pintor et al. |
| 2013/0197622 A1 | 8/2013 | Mitra et al. |
| 2013/0211508 A1 | 8/2013 | Lane et al. |
| 2013/0253635 A1 | 9/2013 | Straubinger et al. |
| 2013/0253642 A1 | 9/2013 | Brecker |
| 2013/0310928 A1 | 11/2013 | Morriss et al. |
| 2013/0331929 A1 | 12/2013 | Mitra et al. |
| 2013/0338766 A1 | 12/2013 | Hastings et al. |
| 2013/0345786 A1 | 12/2013 | Behan |
| 2014/0018912 A1 | 1/2014 | Delaloye et al. |
| 2014/0025163 A1 | 1/2014 | Padala et al. |
| 2014/0039611 A1 | 2/2014 | Lane et al. |
| 2014/0052237 A1 | 2/2014 | Lane et al. |
| 2014/0100651 A1 | 4/2014 | Kheradvar et al. |
| 2014/0107767 A1* | 4/2014 | Braido .................. A61B 50/30 623/2.11 |
| 2014/0163668 A1 | 6/2014 | Rafiee |
| 2014/0172077 A1 | 6/2014 | Bruchman et al. |
| 2014/0172083 A1 | 6/2014 | Bruchman et al. |
| 2014/0194981 A1 | 7/2014 | Menk et al. |
| 2014/0207231 A1 | 7/2014 | Hacohen et al. |
| 2014/0214157 A1 | 7/2014 | Börtlein et al. |
| 2014/0222136 A1 | 8/2014 | Geist et al. |
| 2014/0222139 A1 | 8/2014 | Nguyen et al. |
| 2014/0222142 A1 | 8/2014 | Kovalsky et al. |
| 2014/0222144 A1 | 8/2014 | Eberhardt et al. |
| 2014/0243966 A1 | 8/2014 | Garde et al. |
| 2014/0257467 A1 | 9/2014 | Lane et al. |
| 2014/0277390 A1 | 9/2014 | Ratz et al. |
| 2014/0277412 A1 | 9/2014 | Börtlein et al. |
| 2014/0277422 A1 | 9/2014 | Ratz et al. |
| 2014/0277426 A1 | 9/2014 | Dakin et al. |
| 2014/0277427 A1 | 9/2014 | Ratz et al. |
| 2014/0296973 A1 | 10/2014 | Bergheim et al. |
| 2014/0296975 A1 | 10/2014 | Tegels et al. |
| 2014/0303719 A1 | 10/2014 | Cox et al. |
| 2014/0309728 A1 | 10/2014 | Dehdashtian et al. |
| 2014/0324160 A1 | 10/2014 | Benichou et al. |
| 2014/0324164 A1 | 10/2014 | Gross et al. |
| 2014/0330368 A1 | 11/2014 | Gloss et al. |
| 2014/0330371 A1 | 11/2014 | Gloss et al. |
| 2014/0330372 A1 | 11/2014 | Weston et al. |
| 2014/0336754 A1 | 11/2014 | Gurskis et al. |
| 2014/0343669 A1 | 11/2014 | Lane et al. |
| 2014/0343670 A1 | 11/2014 | Bakis et al. |
| 2014/0350666 A1 | 11/2014 | Righini |
| 2014/0350668 A1 | 11/2014 | Delaloye et al. |
| 2014/0358223 A1 | 12/2014 | Rafiee et al. |
| 2014/0364939 A1 | 12/2014 | Deshmukh et al. |
| 2014/0364943 A1 | 12/2014 | Conklin |
| 2014/0371842 A1 | 12/2014 | Marquez et al. |
| 2014/0371844 A1 | 12/2014 | Dale et al. |
| 2014/0371847 A1 | 12/2014 | Madrid et al. |
| 2014/0371848 A1 | 12/2014 | Murray et al. |
| 2015/0005863 A1 | 1/2015 | Para |
| 2015/0018944 A1 | 1/2015 | O'Connell et al. |
| 2015/0039083 A1 | 2/2015 | Rafiee |

(56) References Cited

U.S. PATENT DOCUMENTS

| | | |
|---|---|---|
| 2015/0142103 A1 | 5/2015 | Vidlund |
| 2015/0148731 A1 | 5/2015 | McNamara et al. |
| 2015/0173897 A1 | 6/2015 | Raanani et al. |
| 2015/0196390 A1 | 7/2015 | Ma et al. |
| 2015/0209141 A1 | 7/2015 | Braido et al. |
| 2015/0272737 A1 | 10/2015 | Dale et al. |
| 2015/0297346 A1 | 10/2015 | Duffy et al. |
| 2015/0335429 A1 | 11/2015 | Morriss et al. |
| 2015/0351903 A1 | 12/2015 | Morriss et al. |
| 2015/0359629 A1 | 12/2015 | Ganesan et al. |
| 2016/0000591 A1 | 1/2016 | Lei et al. |
| 2016/0030169 A1 | 2/2016 | Shahriari |
| 2016/0030170 A1 | 2/2016 | Alkhatib et al. |
| 2016/0030171 A1 | 2/2016 | Quijano et al. |
| 2016/0038281 A1 | 2/2016 | Delaloye et al. |
| 2016/0074160 A1 | 3/2016 | Christianson et al. |
| 2016/0106537 A1 | 4/2016 | Christianson et al. |
| 2016/0113765 A1 | 4/2016 | Ganesan et al. |
| 2016/0113768 A1 | 4/2016 | Ganesan et al. |
| 2016/0143732 A1 | 5/2016 | Glimsdale |
| 2016/0158010 A1 | 6/2016 | Lim et al. |
| 2016/0166383 A1 | 6/2016 | Lim et al. |
| 2016/0184097 A1 | 6/2016 | Lim et al. |
| 2016/0199206 A1 | 7/2016 | Lim et al. |
| 2016/0213473 A1 | 7/2016 | Hacohen et al. |
| 2016/0235529 A1 | 8/2016 | Ma et al. |
| 2016/0278923 A1 | 9/2016 | Krans et al. |
| 2016/0279386 A1 | 9/2016 | Dale et al. |
| 2016/0310267 A1 | 10/2016 | Zeng et al. |
| 2017/0079785 A1 | 3/2017 | Li |
| 2017/0128209 A1 | 5/2017 | Morriss et al. |
| 2017/0216023 A1 | 8/2017 | Lane et al. |
| 2017/0216575 A1 | 8/2017 | Asleson et al. |
| 2017/0257902 A1 | 9/2017 | Xing et al. |
| 2017/0258614 A1 | 9/2017 | Griffin |
| 2017/0325945 A1 | 11/2017 | Dale et al. |
| 2017/0325954 A1 | 11/2017 | Perszyk |
| 2017/0333186 A1 | 11/2017 | Spargias |
| 2017/0348096 A1 | 12/2017 | Anderson |
| 2017/0367821 A1 | 12/2017 | Landon et al. |
| 2017/0367823 A1 | 12/2017 | Hariton et al. |
| 2018/0014931 A1 | 1/2018 | Morriss et al. |
| 2018/0021129 A1 | 1/2018 | Peterson et al. |
| 2018/0055629 A1 | 3/2018 | Oba et al. |
| 2018/0055636 A1 | 3/2018 | Valencia et al. |
| 2018/0085218 A1 | 3/2018 | Eidenschink |
| 2018/0110534 A1 | 4/2018 | Gavala et al. |
| 2018/0116790 A1 | 5/2018 | Ratz et al. |
| 2019/0008639 A1 | 1/2019 | Landon et al. |
| 2019/0008640 A1 | 1/2019 | Cooper et al. |
| 2019/0060072 A1 | 2/2019 | Zeng |
| 2019/0262129 A1 | 8/2019 | Cooper et al. |
| 2020/0000579 A1 | 1/2020 | Manash et al. |
| 2020/0108225 A1 | 4/2020 | Jamal et al. |
| 2020/0138572 A1 | 5/2020 | Zhao et al. |
| 2020/0345494 A1 | 11/2020 | Srinimukesh et al. |
| 2020/0352718 A1 | 11/2020 | Rowe et al. |
| 2021/0145576 A1 | 5/2021 | Becerra et al. |
| 2021/0307900 A1 | 10/2021 | Hacohen |
| 2021/0378817 A1 | 12/2021 | Nia et al. |
| 2021/0386544 A1 | 12/2021 | Cooper et al. |
| 2022/0142777 A1 | 5/2022 | Scheinblum et al. |
| 2022/0287836 A1 | 9/2022 | Landon et al. |
| 2022/0346993 A1 | 11/2022 | Srinimukesh et al. |
| 2023/0000624 A1 | 1/2023 | Okabe et al. |
| 2023/0200980 A1 | 6/2023 | Peterson et al. |
| 2023/0218391 A1 | 7/2023 | Dass et al. |
| 2023/0380963 A1 | 11/2023 | Kaufman et al. |
| 2023/0390052 A1 | 12/2023 | Okafor et al. |
| 2023/0404753 A1 | 12/2023 | Luong et al. |
| 2024/0008978 A1 | 1/2024 | Nawalakhe et al. |
| 2024/0091000 A1 | 3/2024 | King et al. |

FOREIGN PATENT DOCUMENTS

| | | |
|---|---|---|
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| DE | 10010074 B4 | 4/2005 |
| DE | 102006052564 B3 | 12/2007 |
| EP | 0144167 A2 | 6/1985 |
| EP | 0103546 B1 | 5/1988 |
| EP | 0592410 B1 | 10/1995 |
| EP | 0850607 A1 | 7/1998 |
| EP | 0597967 B1 | 12/1999 |
| EP | 1057460 A1 | 12/2000 |
| EP | 1088529 A2 | 4/2001 |
| EP | 1469797 A1 | 10/2004 |
| EP | 1259194 B1 | 2/2005 |
| EP | 1171059 B1 | 11/2005 |
| EP | 1255510 B1 | 4/2007 |
| EP | 1239901 B1 | 10/2007 |
| EP | 1849440 A1 | 10/2007 |
| EP | 1570809 B1 | 1/2009 |
| EP | 1472996 B1 | 9/2009 |
| EP | 1653888 B1 | 9/2009 |
| EP | 1935377 B1 | 3/2010 |
| EP | 1369098 B1 | 4/2014 |
| EP | 2124826 B1 | 7/2014 |
| EP | 2745805 B1 | 6/2015 |
| EP | 2749254 B1 | 6/2015 |
| EP | 2918249 A2 | 9/2015 |
| EP | 2168536 B1 | 4/2016 |
| EP | 2413842 B1 | 8/2017 |
| EP | 2446915 B1 | 1/2018 |
| EP | 3057541 B1 | 1/2018 |
| EP | 3037064 B1 | 3/2018 |
| EP | 3046511 B1 | 3/2018 |
| EP | 3142603 B1 | 3/2018 |
| EP | 3075354 B1 | 11/2018 |
| EP | 3184083 B1 | 2/2019 |
| EP | 3417813 B1 | 5/2020 |
| EP | 2777616 B1 | 8/2020 |
| EP | 3139864 B1 | 11/2020 |
| EP | 2750630 B1 | 6/2021 |
| EP | 2777617 B1 | 9/2022 |
| EP | 2948103 B1 | 12/2022 |
| EP | 2967858 B1 | 1/2023 |
| EP | 3570779 B1 | 2/2023 |
| EP | 3294220 B1 | 12/2023 |
| FR | 2788217 A1 | 7/2000 |
| GB | 1264471 A | 2/1972 |
| GB | 1315844 A | 5/1973 |
| GB | 2056023 A | 3/1981 |
| GB | 2398245 A | 8/2004 |
| SU | 1271508 A1 | 11/1986 |
| WO | 1991016041 A1 | 10/1991 |
| WO | 1991017720 A1 | 11/1991 |
| WO | 1992017118 A1 | 10/1992 |
| WO | 1993001768 A1 | 2/1993 |
| WO | 1997024080 A1 | 7/1997 |
| WO | 1998029057 A1 | 7/1998 |
| WO | 1999033414 A1 | 7/1999 |
| WO | 1999040964 A1 | 8/1999 |
| WO | 1999047075 A1 | 9/1999 |
| WO | 2000018333 A1 | 4/2000 |
| WO | 2000041652 A1 | 7/2000 |
| WO | 2000047139 A1 | 8/2000 |
| WO | 2000061034 A1 | 10/2000 |
| WO | 2001028459 A1 | 4/2001 |
| WO | 2001035878 A2 | 5/2001 |
| WO | 2001049213 A2 | 7/2001 |
| WO | 2001054624 A1 | 8/2001 |
| WO | 2001054625 A1 | 8/2001 |
| WO | 2001062189 A1 | 8/2001 |
| WO | 2001064137 A1 | 9/2001 |
| WO | 2001076510 A2 | 10/2001 |

(56) References Cited

FOREIGN PATENT DOCUMENTS

| | | |
|---|---|---|
| WO | 2002036048 A1 | 5/2002 |
| WO | 2003047468 A1 | 6/2003 |
| WO | 2003092554 A1 | 11/2003 |
| WO | 2004030569 A2 | 4/2004 |
| WO | 2005011534 A1 | 2/2005 |
| WO | 2005034812 A1 | 4/2005 |
| WO | 2005087140 A1 | 9/2005 |
| WO | 2005102015 A2 | 11/2005 |
| WO | 2006014233 A2 | 2/2006 |
| WO | 2006034008 A2 | 3/2006 |
| WO | 2006085225 A1 | 8/2006 |
| WO | 2006108090 A2 | 10/2006 |
| WO | 2006111391 A1 | 10/2006 |
| WO | 2006138173 A2 | 12/2006 |
| WO | 2007025028 A1 | 3/2007 |
| WO | 2008005405 A2 | 1/2008 |
| WO | 2008035337 A2 | 3/2008 |
| WO | 2008125153 A1 | 10/2008 |
| WO | 2008147964 A1 | 12/2008 |
| WO | 2008150529 A1 | 12/2008 |
| WO | 2009024859 A2 | 2/2009 |
| WO | 2009026563 A2 | 2/2009 |
| WO | 2009042196 A2 | 4/2009 |
| WO | 2009091509 A1 | 7/2009 |
| WO | 2009094500 A1 | 7/2009 |
| WO | 2010005524 A2 | 1/2010 |
| WO | 2010008549 A1 | 1/2010 |
| WO | 2010121076 A2 | 10/2010 |
| WO | 2011002996 A2 | 1/2011 |
| WO | 2011081997 A1 | 7/2011 |
| WO | 2012032187 A1 | 3/2012 |
| WO | 2012095455 A2 | 7/2012 |
| WO | 2013028387 A2 | 2/2013 |
| WO | 2013106585 A1 | 7/2013 |
| WO | 2014018432 A2 | 1/2014 |
| WO | 2014079291 A1 | 5/2014 |
| WO | 2014145338 A1 | 9/2014 |
| WO | 2014149865 A1 | 9/2014 |
| WO | 2014163706 A1 | 10/2014 |
| WO | 2014194178 A1 | 12/2014 |
| WO | 2015057407 A1 | 4/2015 |
| WO | 2015077274 A1 | 5/2015 |
| WO | 2016016899 A1 | 2/2016 |
| WO | 2017035487 A1 | 3/2017 |
| WO | 2018213209 A1 | 11/2018 |
| WO | 2022002054 A1 | 1/2022 |
| WO | 2023006048 A1 | 2/2023 |
| WO | 2023076103 A1 | 5/2023 |
| WO | 2023081236 A1 | 5/2023 |
| WO | 2023091769 A1 | 5/2023 |
| WO | 2023096804 A1 | 6/2023 |
| WO | 2023154250 A1 | 8/2023 |
| WO | 2023196150 A1 | 10/2023 |
| WO | 2023244454 A1 | 12/2023 |
| WO | 2023244767 A1 | 12/2023 |
| WO | 2023250114 A1 | 12/2023 |
| WO | 2024001789 A1 | 1/2024 |
| WO | 2024003620 A1 | 1/2024 |
| WO | 2024007575 A1 | 1/2024 |
| WO | 2024009540 A1 | 1/2024 |
| WO | 2024010739 A1 | 1/2024 |
| WO | 2024030520 A1 | 2/2024 |

OTHER PUBLICATIONS

Andersen, Henning Rud, "History of Percutaneous Aortic Valve Prosthesis," Herz 34 2009 Nr. 5, Urban&Vogel, pp. 343-346, Skejby University Hospital Department of Cardiology, Aarhus, Denmark.
Dotter, M.D., Charles T., "Transluminal Treatment of Arteriosclerotic Obstruction," University of Oregon's Minthorn Memorial Laboratory for Cardiovascular Research through Radiology, Circulation, vol. XXX, Nov. 1964, pp. 654-670.
Inoue, M.D., Kanji, et al., "Clinical Application of Transvenous Mitral Commissurotomy by a New Balloon Catheter," The Journal of Thoracic and Cardiovascular Surgery 87:394-402, 1984.
Pavcnik, M.D., Ph.D., Dusan, et al. "Development and Initial Experimental Evaluation of a Prosthetic Aortic Valve for Transcatheter Placement," Cardiovascular Radiology 1992; 183: 151-154.
Rashkind, M.D., William J., "Historical Aspects of Interventional Cardiology: Past, Present, Future," Texas Heart Institute Journal, Interventional Cardiology, pp. 363-367.
Rösch, M.D., Josef, "The Birth, Early Years and Future of Interventional Radiology," J Vasc Interv Radiol 2003; 14:841-853.
Ross, F.R.C.S., D.N., "Aortic Valve Surgery," Guy's Hospital, London, pp. 192-197, approximately 1968.
Sabbah, Ph.D., Hani N., et al., "Mechanical Factors in the Degeneration of Porcine Bioprosthetic Valves: An Overview," Journal of Cardiac Surgery, vol. 4, No. 4, pp. 302-309, Dec. 1989; ISSN 0886-0440.
Wheatley, M.D., David J., "Valve Prostheses," Rob&Smith's Operative Surgery, Fourth Edition, pp. 415-424, Butterworths 1986.
Bavaria, Joseph E. M.D et al.: "Transcatheter Mitral Valve Implantation: The Future Gold Standard for MR?"
Backer, Ole De, MD, et al., "Percutaneous Transcatheter Mitral Valve Replacement—An Overview of Devices in Preclinical and Early Clinical Evaluation," Contemporary Reviews in Interventional Cardiology, Circ Cardiovasc Interv. 2014;7:400-409.
Bavaria, Joseph E. M.D.: "CardiAQ Valve Technologies: Transcatheter Mitral Valve Implantation," Sep. 21, 2009.
Berreklouw, Eric, PhD, et al., "Sutureless Mitral Valve Replacement With Bioprostheses and Nitinol Attachment Rings: Feasibility in Acute Pig Experiments," The Journal of Thoracic and Cardiovascular Surgery, vol. 142, No. 2, Aug. 2011 in 7 pages.
Boudjemline, Younes, et al., "Steps Toward the Percutaneous Replacement of Atrioventricular Valves," JACC, vol. 46, No. 2, Jul. 19, 2005:360-5.
CardiAQ Valve Technologies, "Innovations in Heart Valve Therapy," In3 San Francisco, Jun. 18, 2008, PowerPoint presentation in 19 slides.
Chiam, Paul T.L., et al., "Percutaneous Transcatheter Aortic Valve Implantation: Assessing Results, Judging Outcomes, and Planning Trials," JACC: Cardiovascular Interventions, The American College of Cardiology Foundation, vol. 1, No. 4, Aug. 2008:341-50.
Condado, Jose Antonio, et al., "Percutaneous Treatment of Heart Valves," Rev Esp Cardio. 2006;59(12):1225-31.
Feldman, Ted, MD. "Prospects for Percutaneous Valve Therapies," Circulation 2007;116:2866-2877.
Fitzgerald, Peter J. M.D., "Tomorrow's Technology: Percutaneous Mitral Valve Replacement, Chordal Shortening, and Beyond," Transcatheter Valve Therapies (TVT) Conference. Seattle, WA.
Fornell, Dave, "Transcatheter Mitral Valve replacement Devices in Development," Diagnostic and Interventional Cardiology, Dec. 30, 2014, p. 3, <http://www.dicardiology.com/article/transcatheter-mitral-valve-replacement-devices-development>.
Grube, E. et al., "Percutaneous aortic valve replacement for severe aortic stenosis in high-risk patients using the second- and current third-generation self-expanding CoreValve prosthesis: device success and 30-day clinical outcome." J Am Coll Cardiol. Jul. 3, 2007;50(1):69-76. Epub Jun. 6, 2007.
Karimi, Houshang, et al., "Percutaneous Valve Therapies," SIS 2007 Yearbook, Chapter 11, pp. 1-11.
Kronemyer, Bob, "CardiAQ Valve Technologies: Percutaneous Mitral Valve Replacement," Start Up—Windhover Review of Emerging Medical Ventures, vol. 14, Issue No. 6, Jun. 2009, pp. 48-49.
Leon, Martin B., et al., "Transcatheter Aortic Valve Replacement in Patients with Critical Aortic Stenosis: Rationale, Device Descriptions, Early Clinical Experiences, and Perspectives," Semin. Thorac. Cardiovasc. Surg. 18:165-174, 2006 in 10 pages.
Lutter, Georg, et al., "Off-Pump Transapical Mitral Valve Replacement," European Journal of Cardio-thoracic Surgery 36 (2009) 124-128.
Ma, Liang, et al., "Double-Crowned Valved Stents for Off-Pump Mitral Valve Replacement," European Journal of Cardio-thoracic Surgery 28 (2005) 194-199.
Mack, Michael, M.D., "Antegrade Transcatheter Mitral valve Implantation: A Short-term Experience in Swine Model,".

(56) References Cited

OTHER PUBLICATIONS

Mack, Michael, M.D., "Antegrade Transcatheter Mitral valve Implantation: On-Going Experience in Swine Model,".
Ostrovsky, Gene, "Transcatheter Mitral Valve Implantation Technology from CardiAQ," medGadget, Jan. 15, 2010, available at: http://www.medgadget.com/2010/01/transcatheter_mitral_valve_implantation_technology_from_cardiaq.html.
Preston-Maher, Georgia L., et al., "A Technical Review of Minimally Invasive Mitral Valve Replacements," Cardiovascular Engineering and Technology, vol. 6, No. 2, Jun. 2015, pp. 174-184.
Quadri, Arshad M.D., "Transcatheter Mitral Valve Implantation (TMVI) (An Acute in Vivo Study),".
Ratz, J. Brent, "LSI EMT Spotlight," May 15, 2009.
Ratz, J. Brent et al., "Any experiences making an expandable stent frame?" Arch-Pub.com, Architecture Forums: Modeling, Multiple forum postings from Feb. 3, 2009 to Feb. 4, 2009, http://www.archpub.com.
Ratz, J. Brent, "In3 Company Overview," Jun. 24, 2009.
Ruiz, Carlos E., "Overview of Novel Transcatheter Valve Technologies,".
Spillner, J. et al., "New Sutureless 'Atrial- Mitral-Valve Prosthesis' For Minimally Invasive Mitral Valve Therapy," Textile Research Journal, 2010, in 7 pages.
Sondergaard, Lars, et al., "Transcatheter Mitral Valve Implantation: CardiAQ™," TCT 2013.
Sondergaard, Lars, et al., "Transcatheter Mitral Valve Implantation: CardiAQ™," EuroPCR 2013.
Sondergaard, Lars, "CardiAQ TMVR FIH—Generation 2," TVT symposium.
Treede et al.: "Transapical transcatheter aortic valve implantation using the JenaValve™ system: acute and 30-day results of the multicentre CE-mark study." http://ejcts.oxfordjournals.org/content/41/6/e131.long. Apr. 16, 2012.
Taramasso et al.: "New devices for TAVI: technologies and initial clinical experiences" http://www.nature.com/nrcardio/journal/v11/n3/full/nrcardio.2013.221.html?message-global=remove#access. Jan. 21, 2014.
Webb, John G., et al., "Transcatheter Aortic Valve Implantation: The Evolution of Prostheses, Delivery Systems and Approaches," Archives of Cardiovascular Disease (2012) 105, 153-159.
Wayback Machine, Cleveland Clinic Lerner Research Institute, Transcatheter Mitral Stent/Valve Prosthetic, https://web.archive.org/web/20130831094624/http://mds.clevelandclinic.org/Portfolio.aspx?n=331, indicated as archived on Aug. 31, 2013.
"CardiAQ Valve Technologies, Percutaneous Mitral Valve Replacement, Company Overview," at TVT on Jun. 25, 2009.
BioSpace, "CardiAQ Valve Technologies (CVT) Reports First-In-Human Percutaneous Transfemoral, Transseptal Implantation With Its Second Generation Transcatheter Bioprosthetic Mitral Heart Valve," Jun. 23, 2015, p. 1, http://www.biospace.com/News/cardiaq-valve-technologies-cvt-reports-first- in/382370.
BioSpace, "CardiAQ Valve Technologies (CVT) Reports Cardiovascular Medicine Milestone: First-In-Humannonsurgical Percutaneous Implantation of a Bioprosthetic Mitral Heart Valve," Jun. 14, 2012, p. 1, http://www.biospace.com/News/cardiaq-valve-technologies-cvt-reports/263900.
Neovasc corporate presentation, Oct. 2009, available at http://www.neovasc.com/investors/documents/Neovasc-Corporate-Presentation-October-2009.pdf.

\* cited by examiner

STORAGE JAR ASSEMBLY FOR A PROSTHETIC HEART VALVE

CROSS REFERENCE TO RELATED APPLICATIONS

This application is a continuation of PCT Application No. PCT/US2021/062690, filed on Dec. 9, 2021, which claims the benefit of U.S. Provisional Patent Application No. 63/199,331, filed on Dec. 18, 2020, both of which applications are incorporated herein by reference in their entirety.

FIELD

The present disclosure relates to a storage jar assembly that is configured to receive a prosthetic heart valve.

BACKGROUND

The human heart can suffer from various valvular diseases. These valvular diseases can result in significant malfunctioning of the heart and ultimately require repair of the native valve or replacement of the native valve with an artificial valve. Transcatheter prosthetic heart valves are designed with an expandable frame and a valvular structure (e.g., one or more prosthetic leaflets) attached to the frame. This configuration allows the prosthetic heart valve to be inserted in a patient while compressed or partially compressed, and then to be expanded to fit the diameter of the native heart valve being replaced.

In some cases, the prosthetic leaflets, typically made of pericardial tissues, require hydration when they are stored prior to use. The prosthetic heart valve must also be protected from physical damage during shipping and storage. This is generally accomplished by the use of a valve storage jar assembly containing a hydrating fluid, such as glutaraldehyde, allowing the storage jar assembly to both physically protect and hydrate the leaflets of the prosthetic heart valve before it is installed in a patient.

Typically, a prosthetic heart valve is placed loose in a jar and therefore can be exposed to potential damage during storage, shipping and handling through contact between the prosthetic heart valve and the inner surfaces of the jar. Additionally, during device preparation, removal of the prosthetic heart valve from the jar can be awkward or difficult to accomplish because the clinician must reach into the jar with a sterile tool, such as forceps or tweezers, while avoiding contact the sides of the jar and avoiding pinching or tearing of the soft components of the prosthetic heart valve.

Known storage jar assemblies have included a valve holding mechanism for holding a prosthetic valve within a jar. The valve holding mechanism requires the placement of sutures for securing the prosthetic valve to the valve holding mechanism during the assembly process. As can be appreciated, this increases the complexity and length of the assembly process. Moreover, special tools may be required to remove the valve holding mechanism and the prosthetic valve from the jar as well as to remove the prosthetic valve from the valve holding mechanism.

Another issue concerning storage jar assemblies is that prosthetic heart valves come in various sizes. A storage jar assembly designed for a prosthetic heart valve of one specific size may not be suitable for use with a similar valve of a different size.

Therefore, there is a need for storage jars assemblies for prosthetic heart valves that overcome one or more disadvantages of the prior art.

SUMMARY

Disclosed herein are prosthetic heart valves, storage jar assemblies for use with various prosthetic heart valves, as well as securing devices for securing or holding prosthetic heart valves inside storage jar assemblies during shipping, storage, and subsequent handling. The securing devices can be used to partially compress prosthetic heart valves so that they may be contained in the storage jar assemblies disclosed herein. In some embodiments, the securing device is attached to or incorporated in a lid of the storage jar assembly. In other embodiments, the securing device may be a holder that can be inserted into the storage jar assembly.

Certain embodiments of the disclosure concern a storage jar assembly including a jar having an open end and configured to receive a prosthetic heart valve. Such embodiments also include a lid configured to cover the open end of the jar. The lid can include a plurality of valve attachment features configured to be releasably attached to corresponding features of the prosthetic heart valve.

Certain embodiments of the disclosure concern another storage jar assembly including a jar having an open end and configured to receive a prosthetic heart valve. Such embodiments also include a lid configured to cover the open end of the jar. Such embodiments also include a valve securement mechanism coupled to the lid and comprising a plurality of notches configured to be releasably attached to corresponding features of the prosthetic heart valve and hold one end of the prosthetic heart valve in at least a partially radially compressed state.

Certain embodiments of the disclosure concern another storage jar assembly including a jar having an open end and configured to receive a prosthetic heart valve. Such embodiments also include a lid configured to cover the open end of the jar and a valve holder. The valve holder can comprise a base, a column, and plurality of valve retention members. The column can have a lower end coupled to the base, an upper end, and can extend axially from the base. The plurality of valve retention members can extend upwardly from the base and can be configured to contact an outer surface of the prosthetic heart valve.

Certain embodiments of the disclosure concern another storage jar assembly including a jar having an open end and configured to receive a prosthetic heart valve. Such embodiments also include a lid configured to cover the open end of the jar and a valve holder configured to hold the prosthetic heart valve in a partially compressed state within the jar.

Certain embodiments of the disclosure concern a lid, configured to cover an open end of a jar to form a storage jar assembly. The lid also includes an upper portion, a side wall depending from the upper portion, and a valve attachment feature coupled to the lid. The valve attachment feature can be configured to releasably hold corresponding features of a prosthetic heart valve. The lid can also include a valve release mechanism configured to detach the prosthetic heart valve from the valve attachment feature.

Certain embodiments of the disclosure concern a storage jar assembly, comprising a jar having an open end and configured to receive a prosthetic heart valve and a lid, configured to cover an open end of the jar. The lid may include an upper portion, a side wall depending from the upper portion, and a valve attachment feature coupled to the lid. The valve attachment mechanism may be configured to releasably hold corresponding features of a prosthetic heart valve. Such embodiments can also include a valve release mechanism configured to detach the prosthetic heart valve from the valve attachment feature.

The foregoing and other objects, features, and advantages of the invention will become more apparent from the following detailed description, which proceeds with reference to the accompanying figures.

DETAILED DESCRIPTION

Disclosed herein are storage jar assemblies comprising securing mechanisms for prosthetic heart valves. Storage jar assemblies disclosed herein generally comprise a jar and a removable lid. The jar is configured to receive a prosthetic heart valve. The prosthetic heart valve rests within the jar when it is being stored and is removed from the jar prior to use. In particular embodiments, the securing mechanisms can hold a prosthetic heart valve in at least a partially-compressed state to permit use of a relatively smaller jar and/or to better secure the prosthetic heart valve within the jar during shipping and storage.

The storage jar assemblies disclosed herein may be used with various embodiments of prosthetic heart valves. Prosthetic heart valves for use with the presently disclosed storage jar assemblies can have a frame assembly comprising at least one radially compressible and expandable frame and a valvular structure supported within the frame assembly. Additionally, the prosthetic heart valves may have a plurality of anchoring structures for securing the prosthetic heart valve to native tissue of a patient. In some embodiments, the frame assembly can comprise an inner frame and an outer frame.

Figure 1:
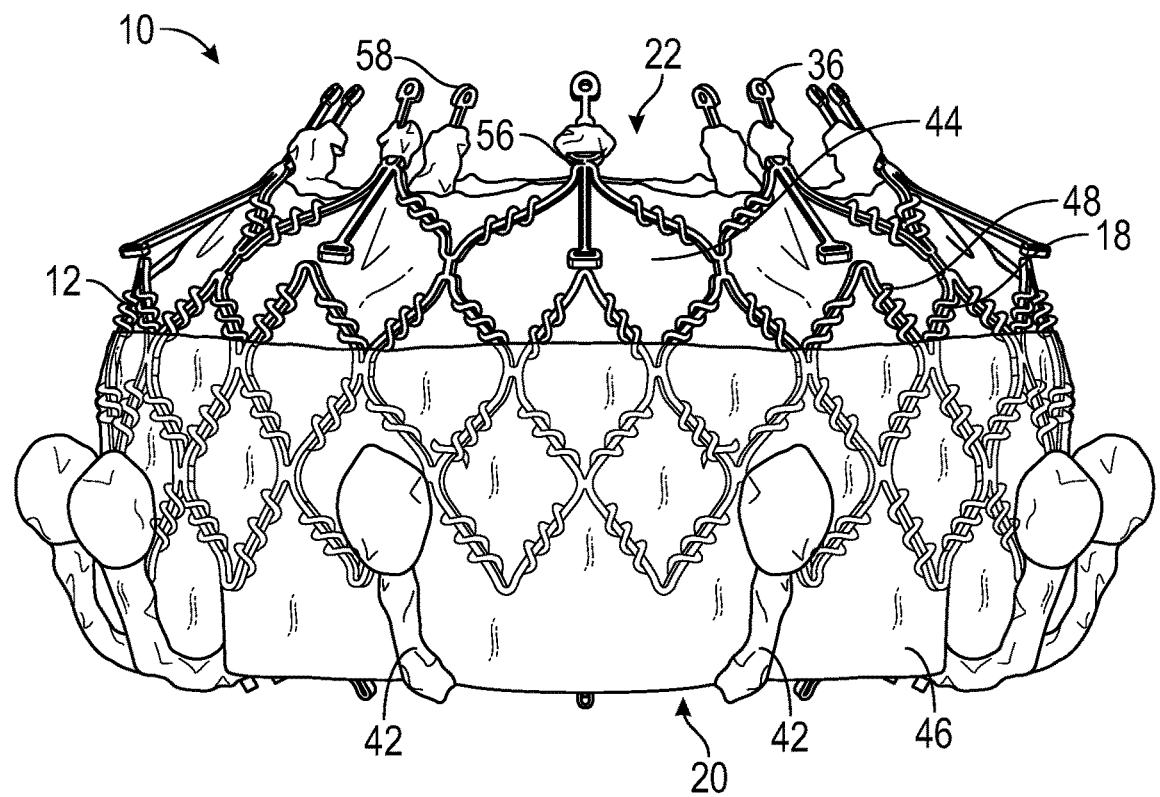
FIG. 1 is a perspective view of a prosthetic heart valve, according to one embodiment.
Figure 2:
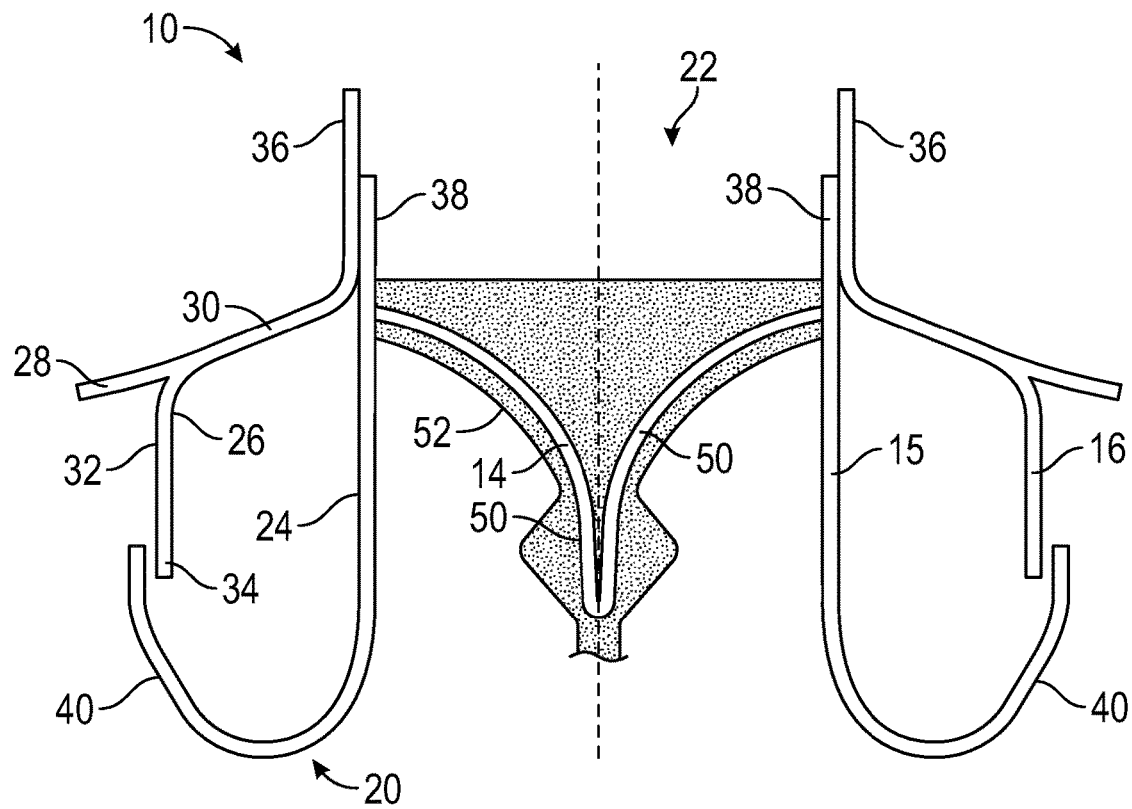
FIG. 2 is a cross sectional schematic view of the frame and valvular structure of the prosthetic heart valve of FIG. 1.

For example, FIGS. 1 and 2 depict one embodiment of a prosthetic heart valve 10 that can be used with the storage jar assemblies disclosed herein. The prosthetic heart valve 10 comprises a frame assembly 12 and a valvular structure 14 supported by the frame assembly 12. The frame assembly 12 defines an inlet end 22 and an outlet end 20 of the prosthetic heart valve 10. As best shown in FIG. 2, the frame assembly 12 in the illustrated embodiment includes an inner frame 15 and an outer frame 16. The inner and outer frames 15, 16 can comprises a plurality of interconnected struts 18 arranged in a lattice or diamond pattern.

The inner frame 15 can include an annular inner frame body 24. The inner frame body 24 can have a generally cylindrical shape such that it has a substantially constant diameter from an upper end (inlet end) to a lower end (outlet end) of the inner frame body 24. However, it is to be understood that in alternative embodiments, the diameter of the inner frame body 24 can vary along its length. Although inner frame body 24 is described as generally having a cylindrical shape, it is understood that all or a portion of the inner frame body 24 can have a non-circular cross-section such as, but not limited to, a D-shape.

The outer frame 16 can include an annular outer frame body 26 and an outer frame anchoring feature 28. The outer frame body 26 can have an upper region 30, an intermediate region 32, and a lower region 34. In some situations, such as those in which the prosthetic heart valve 10 is positioned within a native mitral valve, the upper region 30 can be generally positioned supra-annularly, the intermediate region 32 can be generally positioned intra-annularly, and the lower region 34 can be positioned sub-annularly. However, it is to be understood that in some situations, the positioning of the outer frame 16 relative to the annulus can differ. Moreover, it is to be understood that in some embodiments, the outer frame 16 can omit one or more of the upper region 30, the intermediate region 32, and/or the lower region 34.

The outer frame 16 can include a plurality of angularly spaced outer posts 36 extending from the respective apices 56 of the upper region 30 at the inlet end 22 of the prosthetic heart valve. In the illustrated embodiment, FIG. 1 shows the outer frame 16 has ten such posts 36, although a greater or lesser number of posts may be used. As best shown in FIG. 2, the inner frame 15 similarly may include a plurality of angularly spaced inner posts 38, each of which can be circumferentially aligned with a corresponding post 36 of the outer frame 16 to form a plurality of pairs of posts 36, 38 angularly spaced from each other along the inlet end 22. The inner and outer posts 36, 38 of each pair can be connected to each other with a suture and/or a fabric. The outer posts 38 and/or the inner posts 38 can be used to form a releasable connection with a delivery apparatus for securing the prosthetic heart valve 10 to the delivery apparatus when the prosthetic heart valve and the delivery apparatus are advanced through a patient's vasculature to a desired implantation site (e.g., the native mitral valve). The outer posts 38 and/or the inner posts 38 can also be used to form a releasable connection with a securement mechanism of a storage jar assembly, as further described below.

The frame assembly 12 may further include a plurality of angularly spaced anchoring features 40 (which can also be referred to as "anchoring legs" or "ventricular anchors"). The anchoring features 40 can extend from an outflow end of the inner frame body 24. As illustrated in FIG. 1, the anchoring features 40 may extend generally downwardly and radially outwardly from the outlet end of the inner frame body 24. When implanted in a native valve (e.g., a native mitral or tricuspid valve), the anchoring features 40 can extend behind and/or engage native tissue, such as the native leaflets and/or chordae tendineae, within a ventricle of a heart. As shown in FIG. 1, the anchoring features 40 can be covered or wrapped by respective covers 42, which can be formed from a relatively soft material, such as a fabric or natural tissue. In alternative embodiments, the anchoring features 40 can be components of the outer frame 16. For example, the anchoring features 40 can extend from an outlet end of the outer frame main body 26. In alternative embodiments, similar anchoring features can be provided at the inlet of the inner frame 15 or the outer frame 16 for engaging tissue within an atrium of a heart.

The prosthetic heart valve 10 can include one or more skirts for sealing against native tissue surrounding the prosthetic heart valve once implanted, for attaching other components (e.g., leaflets) to the frame assembly and/or for blocking the flow of blood through the open cells of the frame. As shown in FIG. 1, the prosthetic heart valve 10 can have an inner skirt 44 and an outer skirt 46. The inner skirt 44 can be disposed between the inner frame 15 and the outer frame 16 and can be attached to the outer frame 16 by sutures 48. The outer skirt 46 can be disposed around the outer frame 16 and can be attached to the outer frame by sutures 48. In some embodiments, the inner skirt 44 and the outer skirt 46 can be formed from a single piece of material that is folded at one end. In other embodiments, the inner skirt 44 and the outer skirt 46 can be formed from separate pieces of material. The skirts 44, 46 can be made of any of various suitable materials, including synthetic fabrics, such as polyethylene terephthalate (PET) fabric, or natural tissue (e.g., pericardial tissue).

As shown in FIG. 2, the valvular structure 14 may comprise a leaflet assembly comprising a plurality of leaflets 50 disposed within a lumen of the inner frame 15. In particular embodiments, the leaflet assembly comprises three leaflets 50, although a greater or fewer number of leaflets may be used in other embodiments. The leaflets 50 are configured to permit flow from the inlet end 22 of the prosthetic heart valve 10 to the outlet end 20, but to prohibit flow from the outlet end 20 of the prosthetic heart valve 10 to the inlet end. The leaflets 50 can be made of pericardial tissue (e.g., bovine pericardial tissue), biocompatible synthetic materials, or various other suitable natural or synthetic materials as known in the art.

The leaflet assembly can further include a liner 52. The liner 52 can be used to assist with fluid flow through and/or around the prosthetic heart valve 10, such as through the inner frame 15 and the valve leaflets 50. The liner 52 can surround at least a portion of the valve leaflets 50 and be connected to one or more of the valve leaflets 50. For example, as shown in the illustrated embodiment, the one or more valve leaflets 50 can be attached to the liner 52 (e.g., by sutures) along an arcuate or fixed edge of the valve leaflets 50. The liner 52 can extend from the arcuate or fixed edge of each leaflet 50 and extend upwardly towards an upper end of the inner frame 15. The liner 52 in turn can be attached to the inner frame 15, such as by sutures.

The outer frame 16 can be attached to the inner frame 15 at one or more attachment points. The outer frame 16 can be tautly attached to the inner frame 15 such that little to no relative movement between the inner frame 15 and the outer frame 16 occurs at the one or more attachment points. In other embodiments, the outer frame 16 and the inner frame 15 can be loosely attached such that some relative movement between the inner frame 15 and the outer frame 16 can occur at the one or more attachment points. Although the outer frame 16 and inner frame 15 are illustrated as separate components in FIG. 2, it is to be understood that outer frame 16 and inner frame 15 can be unitarily or monolithically formed. For example, the entire frame assembly 12 can be formed (e.g., laser cut) from a single piece of material.

In alternative embodiments, the prosthetic heart valve 10 can have a single frame, which can be formed with the outer posts 36, anchoring features 40, and/or other features described above in connection with frames 15 and 16. Examples of a prosthetic heart valve having a single frame are disclosed in Publication No. US 2016/0317301 and U.S. Pat. No. 10,350,062, which are incorporated herein by reference.

In particular embodiments, the frames 15, 16 are made of a self-expandable material, such as Nitinol. When constructed of a self-expandable material, the frames 15, 16 (and thus the prosthetic heart valve 10) can be crimped to a radially compressed state and restrained in the compressed state by insertion into a sheath or equivalent mechanism of a delivery catheter. Once inside the body at the desired implantation site (e.g., the native mitral valve), the prosthetic heart valve can be advanced from the delivery sheath, which allows the prosthetic heart valve to expand from the radially compressed state to a radially expanded state corresponding to its functional size.

In other embodiments, the frames 15, 16 can be made of any suitable plastically-expandable materials, such as stainless steel or a nickel-based alloy (e.g., a cobalt-chromium or a nickel-cobalt-chromium alloy), polymers, or combinations thereof. When constructed of a plastically-expandable material, the frames 15, 16 (and thus the prosthetic heart valve 10) can be crimped to a radially compressed state on a delivery catheter, such as on or adjacent an inflatable balloon or equivalent expansion mechanism. Once inside the body at the desired implantation site (e.g., the native mitral valve), the prosthetic can be expanded from the radially compressed state to a radially expanded state corresponding to its functional size by the inflatable balloon or the equivalent expansion mechanism.

Exemplary delivery apparatuses that can be used to implant the prosthetic heart valves disclosed herein are disclosed in Publication Nos. US 2016/0317301 and 2019/0008640, which are incorporated herein by reference.

Figure 3:
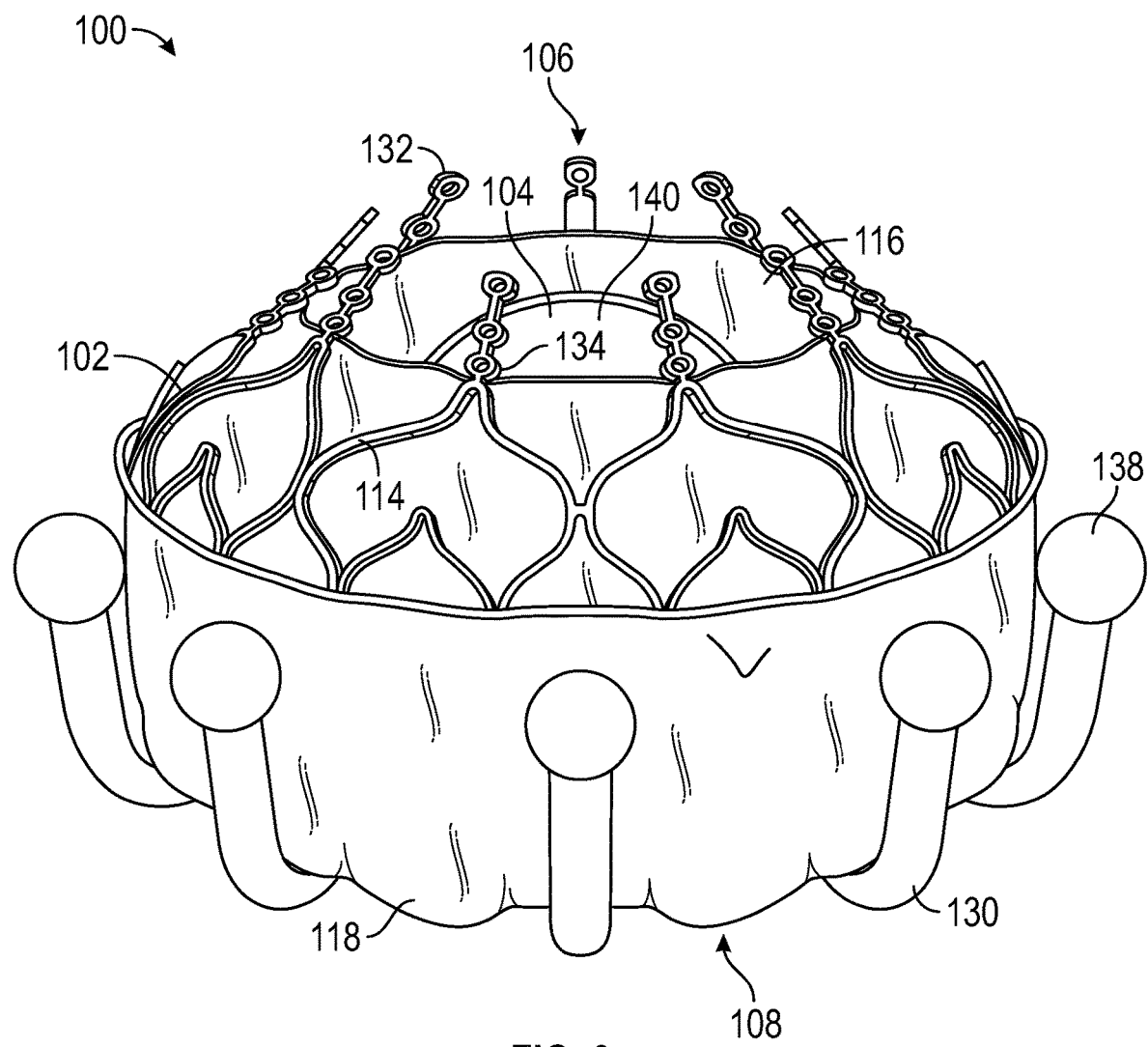
FIG. 3 is a perspective view of a prosthetic heart valve, according to another embodiment.
Figure 4:
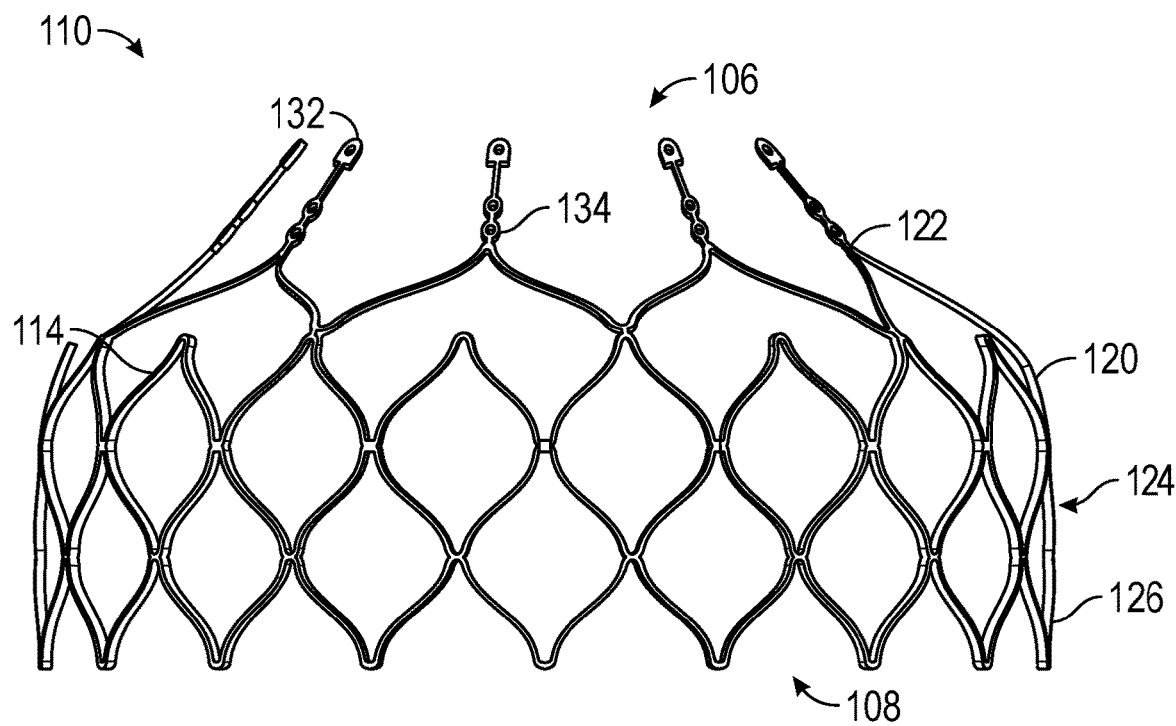
FIG. 4 is a side elevation view of the inner frame of the prosthetic heart valve of FIG. 3.
Figure 5:
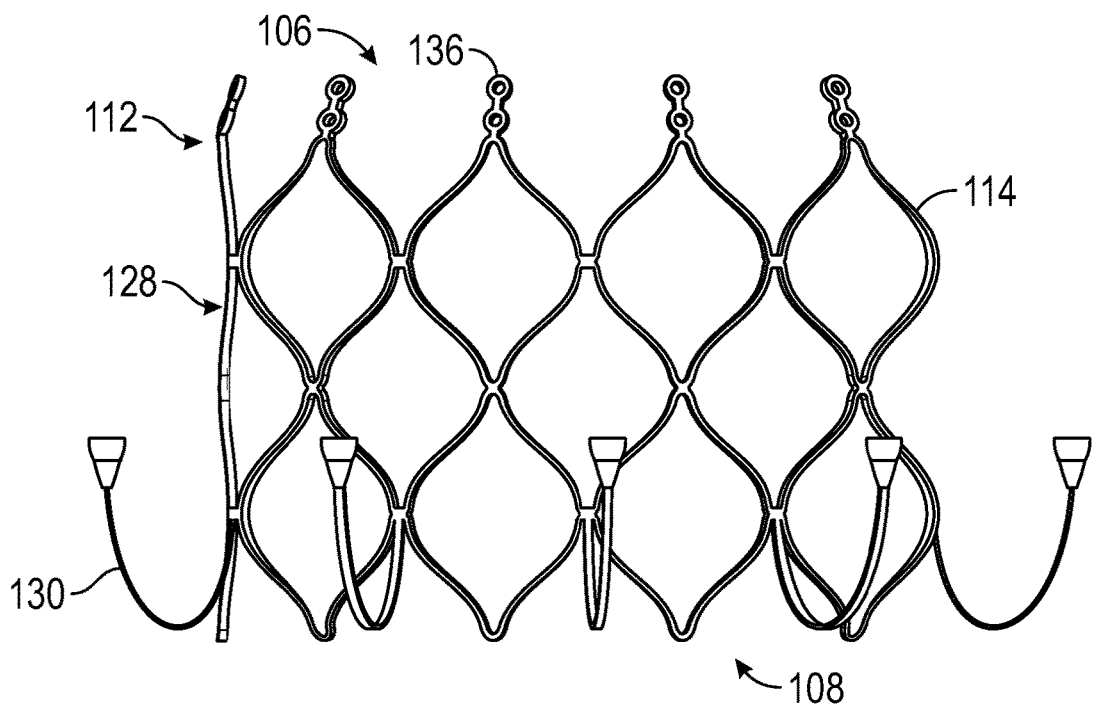
FIG. 5 is a side elevation view of the outer frame of the prosthetic heart valve of FIG. 3.

FIG. 3 depicts an alternative embodiment of a prosthetic heart valve 100 that can be used with the storage jar assemblies disclosed herein. The prosthetic heart valve 100 comprises a frame assembly 102 and a valvular structure 104 supported by the frame 102. The frame assembly 102 defines an inlet end 106 and an outlet end 108 of the prosthetic heart valve 100. As illustrated in FIGS. 4 and 5, the frame assembly 102 in the illustrated embodiment includes an outer frame 110 and an inner frame 112. The outer and inner frames 110, 112 can comprise a plurality of interconnected struts 114 arranged in a lattice or diamond pattern. As shown in FIG. 3, the prosthetic heart valve 100 can also comprise an inner skirt 116 and an outer skirt 118. The skirts 116, 118 may be attached to the frame assembly 102.

As best illustrated in FIG. 4 the outer frame 110 can include an annular outer frame body 120. The outer frame body 120 can have an upper region 122, an intermediate region 124, and a lower region 126. In some situations, such as those in which the prosthetic heart valve 100 is placed within a native mitral valve, the upper region 122 can be generally positioned supra-annularly, the intermediate region 124 can be generally positioned intra-annularly, and the lower region 126 can be generally positioned sub-annularly. However, it is to be understood that in some embodiments, the outer frame 110 can omit one or more of the upper region 122, the intermediate region 124, or the lower region 126.

As best illustrated in FIG. 5, the inner frame 112 can include an annular inner frame body 128 and anchoring features 130. The inner frame body 128 can have a generally cylindrical shape such that it has a substantially constant diameter from an upper end (inlet end) to a lower end (outlet end) of the inner frame body. However, it is to be understood that, in alternative embodiments, the diameter of the inner frame body 128 can vary along its length. Although inner frame body 128 is described as generally having a cylindrical shape, it is understood that all or a portion of the inner frame body 128 may have a non-circular cross-section such as, but not limited to, a D-shaped cross-section.

The outer frame 110 can include a plurality of angularly spaced outer posts 132 extending from respective apices 134 at the upper region 122 near the inlet end 106 of the prosthetic heart valve 100. In one illustrated embodiment, as shown in FIG. 3, the outer frame 110 has eleven such outer posts 132, but a greater or lesser number of posts may be used. As best shown in FIG. 5, inner frame 112 may similarly include a plurality of angularly spaced inner posts 136 along the inlet end 106 of the prosthetic heart valve 100. Each of the angularly spaced inner posts 136 can be circumferentially aligned with a corresponding outer post 132 of the outer frame 110 to form a plurality of pairs of posts 132, 136 angularly spaced from each other along the inlet end 106. The posts 132, 136 of each pair can be connected to each other with a suture and/or a fabric. The outer posts 132 and/or the inner posts 136 can be used to form a resealable connection with a delivery apparatus for securing the prosthetic heart valve 100 to the delivery apparatus when the prosthetic heart valve and delivery apparatus are advanced through a patient's vasculature to a desired implantation site (e.g., the native mitral valve). The outer posts 132 and/or inner posts 136 can also be used to form a releasable connection with a securement mechanism of the storage jar assemblies described herein.

The frame assembly 102 may further include a plurality of angularly spaced anchoring features 130 (which can also be referred to as "anchoring legs" or "ventricular anchors"). The anchoring features 130 can extend from an outflow end of the inner frame body 128. As illustrated in FIG. 3, the anchoring features 130 may extend generally downwardly and radially outwardly from the inner frame body 128. When implanted in a native valve (e.g., a native mitral or tricuspid valve), the anchoring features 130 can extend behind and/or engage native tissue, such as the native leaflets and/or chordae tendineae, within a ventricle of a heart. As shown in FIG. 3, the anchoring features 130 can be covered or wrapped by respective covers 138, which can be formed from a relatively soft material such as fabric or natural tissue. In alternative embodiments, the anchoring features 130 can be components of the outer frame 110. For example, the anchoring features 130 can extend from the lower region 126 of the outer frame body 120. In alternative embodiments, similar anchoring features can be provided at the inlet end of inner frame body 128 or outer frame body 120 for engaging tissue with an atrium of a heart.

The prosthetic heart valve 100 can include one or more skirts for sealing against native tissue surrounding the prosthetic heart valve once implanted, for attaching other components (such as leaflets) to the frame assembly, and/or for blocking the flow of blood through the open cells of the frame. As shown in FIG. 3, the prosthetic heart valve 100 can have an inner skirt 116 and an outer skirt 118. The inner skirt 116 can be disposed between the inner frame 112 and the outer frame 110 and can be attached to the outer frame 110 with sutures or any other suitable attachment mechanism. The outer skirt 118 can be disposed around the outer side of outer frame 110 and can be attached to the outer frame 110 with sutures or any other suitable attachment mechanism. In some embodiments, the inner skirt 116 and outer skirt 118 may be formed from a single piece of material that is folded at one end. In other embodiments, the inner skirt 116 and the outer skirt 118 can be formed from separate pieces of material. The skirts 116, 118 can be made of any suitable materials, including synthetic fabrics or natural tissue.

As shown in FIG. 3, the valvular structure 104 may comprise a plurality of leaflets 140 disposed within a lumen of the inner frame 112. In some embodiments, the valvular structure comprises three leaflets 140, although a greater or fewer number of leaflets may be used in other embodiments. The leaflets 140 are configured to permit flow from inlet end 106 of the prosthetic heart valve 100 to outlet end 108, but to prohibit flow from the outlet end of the prosthetic heart valve 100 to the inlet end 106. The leaflets 140 can be made of pericardial tissue, biocompatible synthetic materials, or synthetic materials as known in the art.

The outer frame 110 can be attached to inner frame 112 at one or more attachment points. The outer frame 110 can be tautly attached to inner frame 112 such that little to no relative movement between the outer frame 110 and the inner frame 112 at the one or more attachment points. In other embodiments, the outer frame 110 and the inner frame 112 can be loosely attached, such that some relative movement between the outer frame 110 and the inner frame 112 can occur at the one or more attachment points. Although the outer frame 110 and the inner frame 112 are illustrated as separate components in FIGS. 4 and 5, it is to be understood that the outer frame 110 and the inner frame 112 can be unitarily or monolithically formed. For example, the entire frame assembly 102 can be formed (e.g., laser cut) from a single piece of material or additively manufactured.

In particular embodiments, the frames 110, 112 are made of a self-expandable material, such as Nitinol. When constructed of a self-expandable material, frames 110, 112 (and thus the prosthetic heart valve 100) can be crimped to a radially compressed state and restrained in the compressed state by insertion into a sheath or equivalent mechanism of a delivery catheter. Once inside the body at the desired implementation site (e.g., the native mitral valve), the prosthetic heart valve can be advanced from the delivery sheath, which allows the prosthetic heart valve to expand from the radially compressed state to a radially expanded state corresponding to its functional size.

In other embodiments, the frames 110, 112 can be made of any suitable plastically-expandable materials, such as stainless steel or a nickel-based alloy (e.g., a cobalt-chromium or a nickel-cobalt-chromium alloy), polymers, or combinations thereof. When constructed of a plastically-expandable material, frames 110, 112 (and thus the prosthetic heart valve 100) can be crimped to a radially compressed state on a delivery catheter, such as on or adjacent to an inflatable balloon or equivalent expansion mechanism. Once inside the body at the desired implantation site (e.g., the native mitral valve), the prosthetic can be expanded from the radially compressed state to a radially expanded state corresponding to its functional size by the inflatable balloon or the equivalent expansion mechanism.

Further details of the prosthetic heart valve 10 of FIGS. 1-2, the prosthetic heart valve 100 of FIGS. 3-5, and other prosthetic heart valves that can be used with the storage jar assemblies of the present disclosure are disclosed in Publication Nos. US 2016/0317301, US 2018/0055629 and US 2019/0262129, and U.S. Pat. No. 10,350,062, which are incorporated herein by reference.

In some embodiments, the storage jar assemblies disclosed herein may incorporate a lid having a valve securement mechanism. The valve securement mechanism can have a plurality of valve attachment features configured to releasably attach to corresponding features on a prosthetic heart valve, such as the outer posts 36. In some embodiments, the valve attachment features may be configured to hold the prosthetic heart valve in a partially compressed state. The lid may further comprise a lid attachment mechanism configured to releasably attach to corresponding features on ajar.

Figure 6:
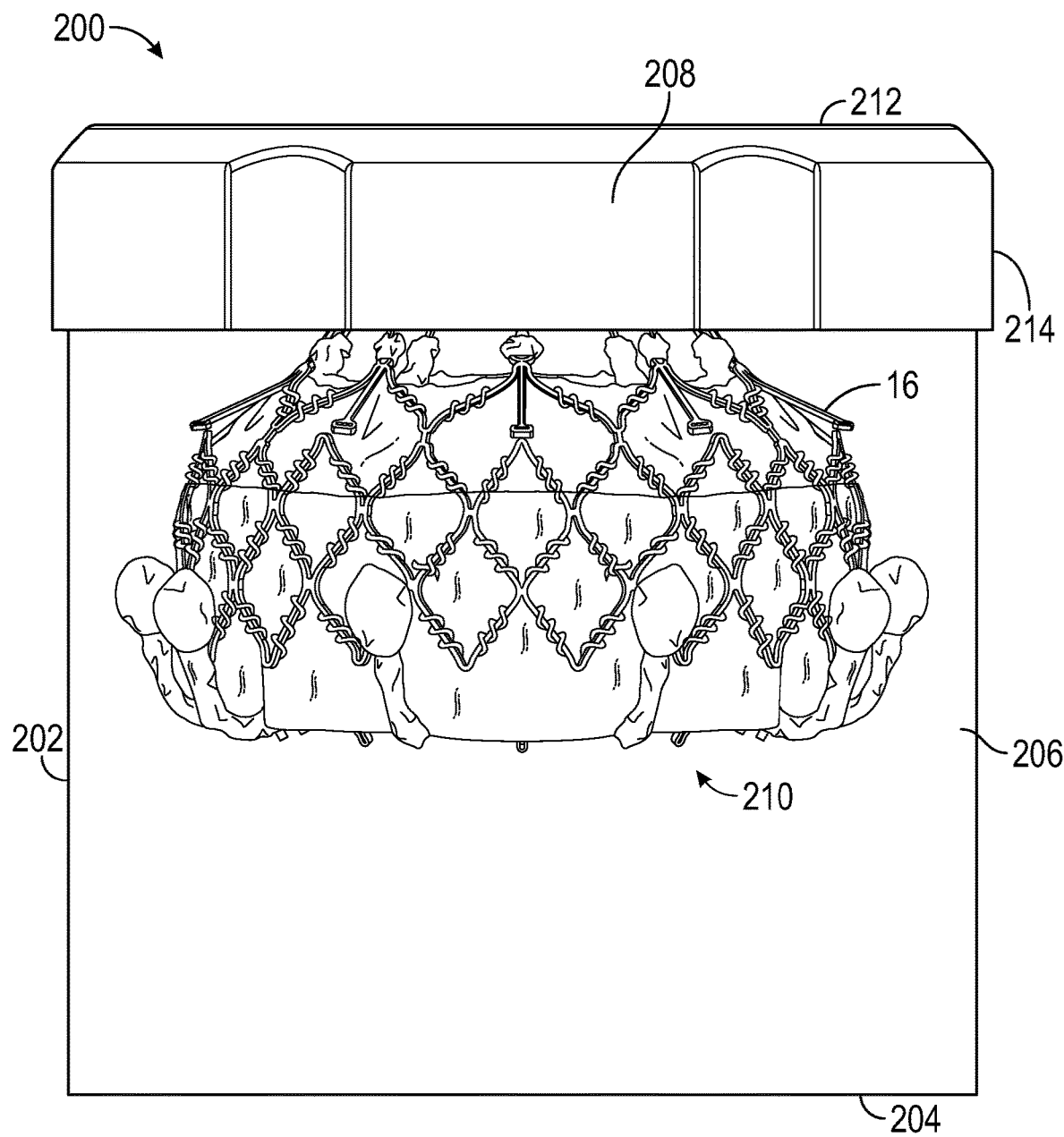
FIG. 6 is a side elevation view of a storage jar assembly containing a prosthetic heart valve attached to a lid of the storage jar assembly, according to one embodiment.

Referring now to the storage jar assembly embodiment shown in FIG. 6, a storage jar assembly 200 can include a jar 202. The jar 202 generally comprises a base 204, an upstanding side wall 206 extending upwardly from the base 204. The upper end portion of the wall 206 can form a mouth defining an opening at the upper end of jar 202. The jar 202 can be configured to receive a prosthetic heart valve, such as prosthetic heart valve 10. Although the following description of the storage jar assembly 200 proceeds with reference to the prosthetic heart valve 10, it should be understood that other prosthetic heart valves (e.g., prosthetic heart valve 100 or any of those disclosed in Publication Nos. US 2016/0317301, US 2018/0055629 and US 2019/0262129, and U.S. Pat. No. 10,350,062) can be used with the storage jar assembly 200.

The storage jar assembly 200 may also have a lid 208 that can be configured to be releasably attachable to the jar 202 and to a prosthetic heart valve 210. The lid 208 may also be configured to hold prosthetic heart valve 210 in a partially-compressed state. In the illustrated embodiment, the jar 202 has a cylindrical wall 206 defining a circular cross-sectional profile (in a plane perpendicular to a central longitudinal axis of the jar). In other embodiments, jar 202 can have plural wall segments that define other cross-sectional profiles (in a plane perpendicular to a central longitudinal axis of the jar), such as square, hexagonal etc.

Figure 7:
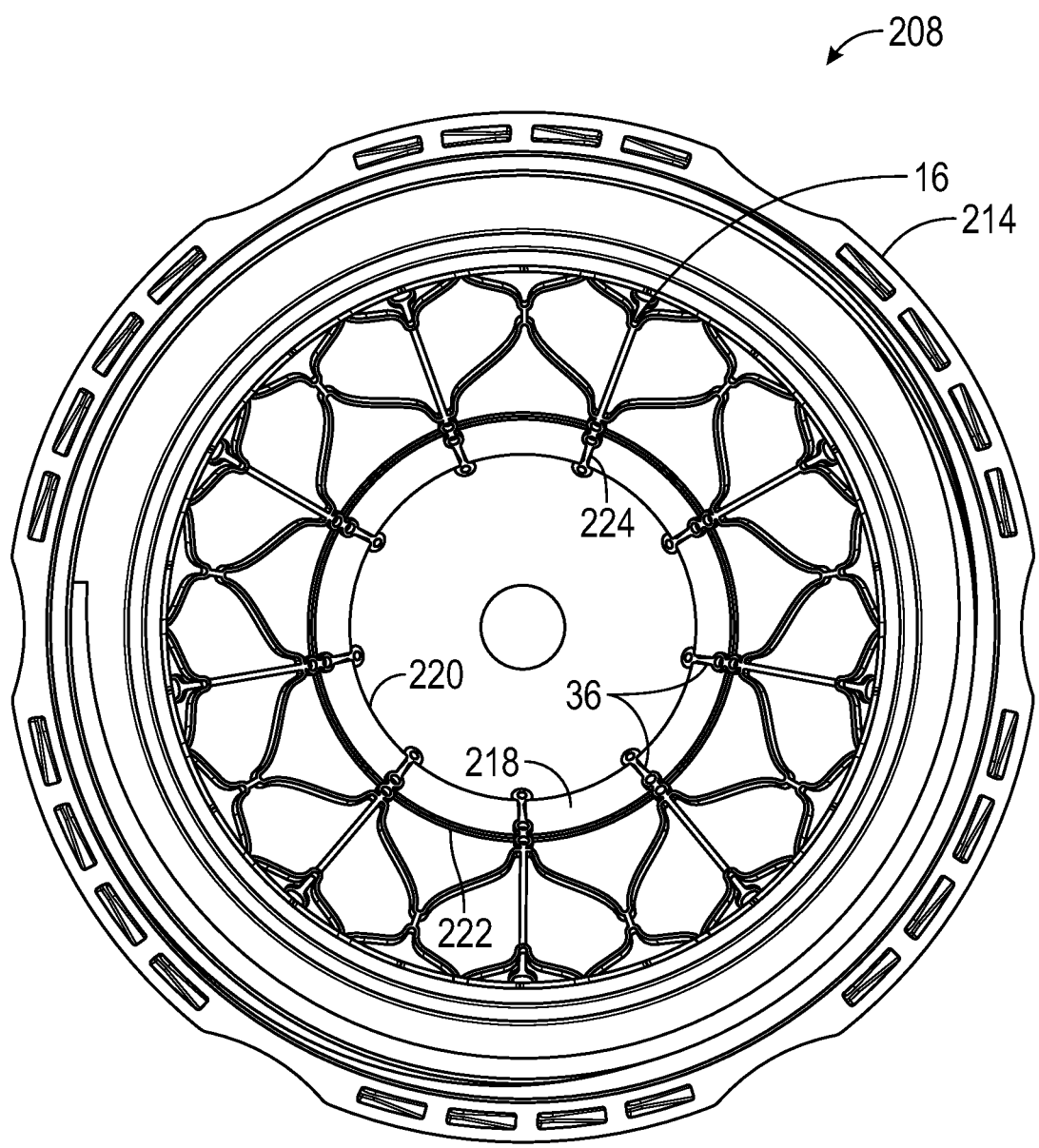
FIG. 7 is a plan view of the bottom of the lid of FIG. 6 showing the outer frame of the prosthetic heart valve attached to the lid.
Figure 8:
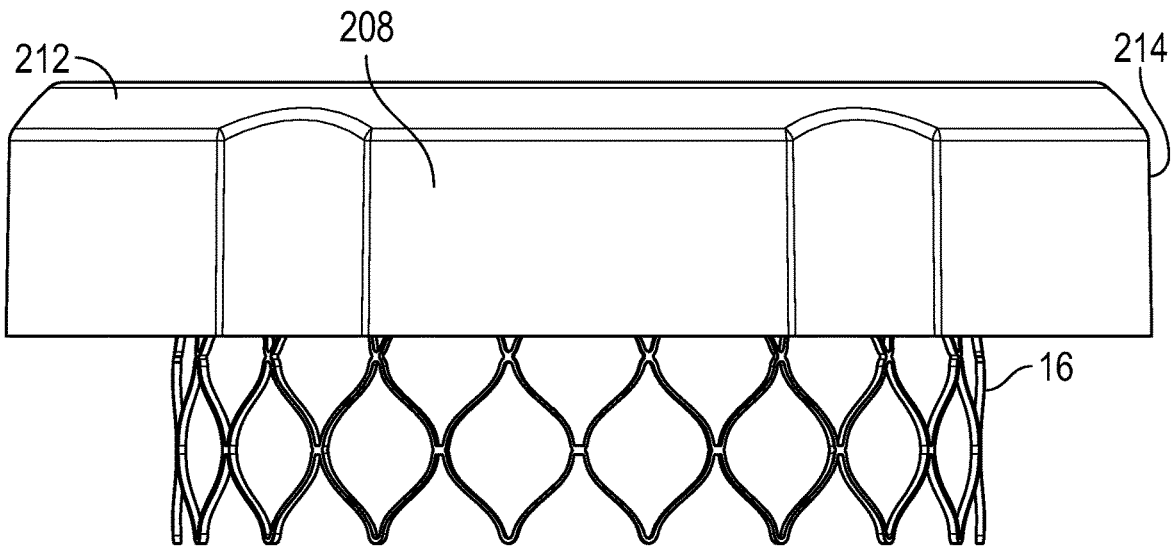
FIG. 8 is a side elevation view of the lid and outer frame shown in FIG. 7.
Figure 9:
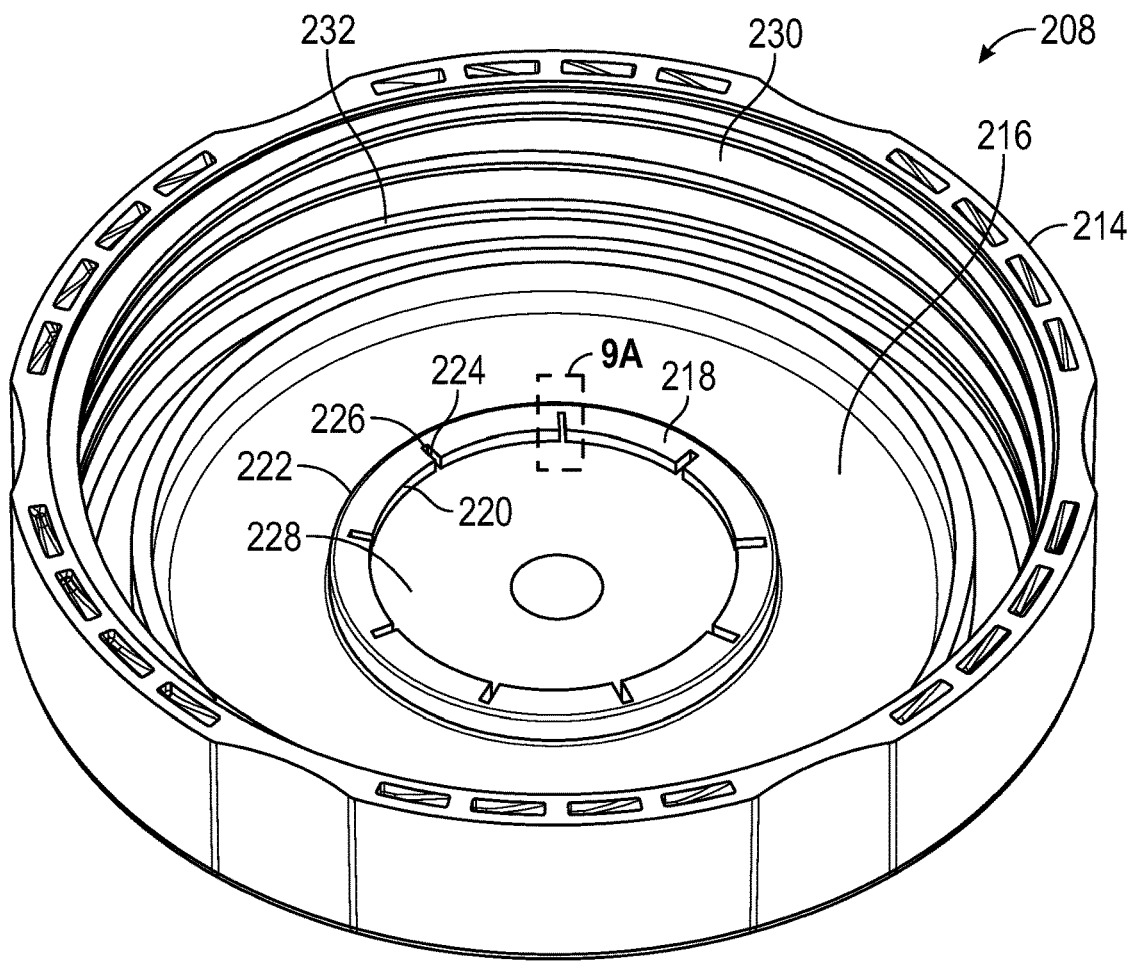
FIG. 9 is a perspective view of the lid shown in FIG. 6.
Figure 10:
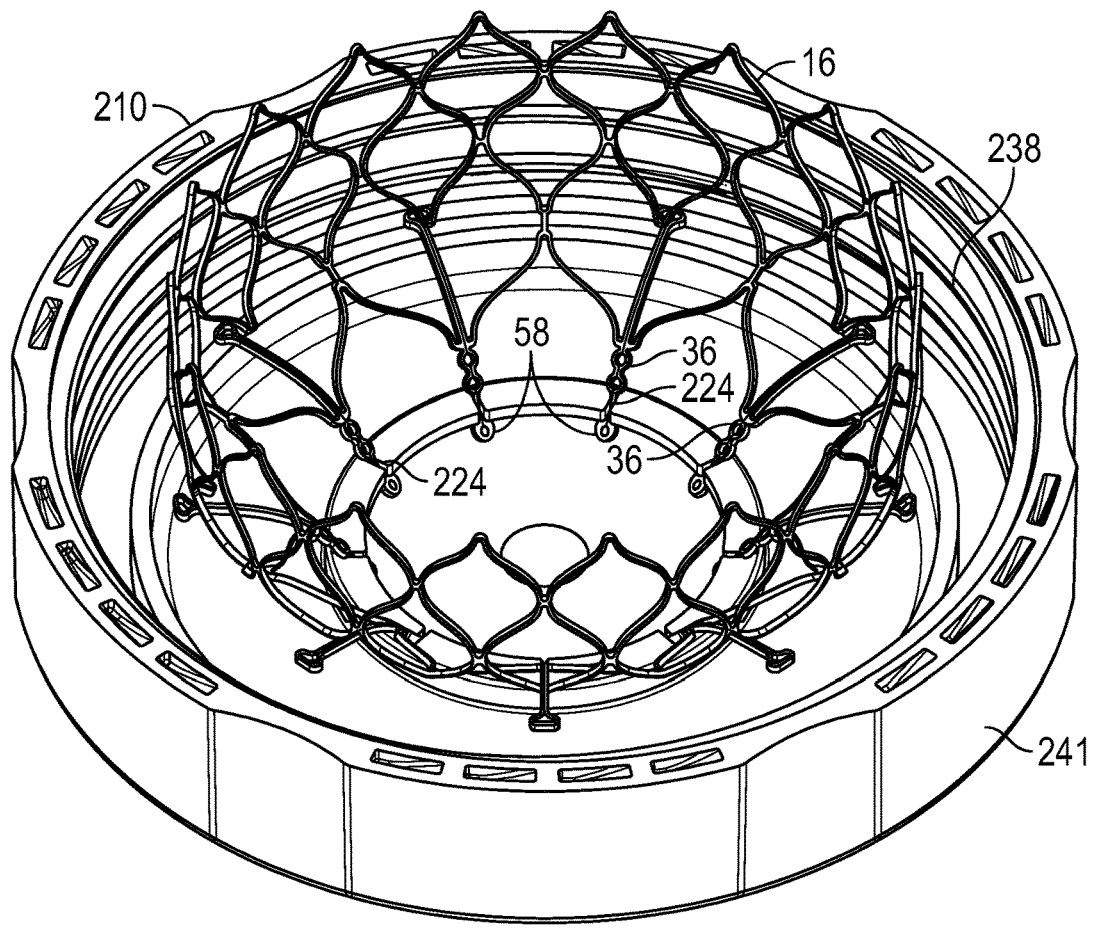
FIG. 10 is a perspective view of the lid and the outer frame of FIG. 7.

Referring to FIGS. 7-10, the lid 208 can have an upper portion 212 and a downwardly depending side wall 214. The inner surface of the lid comprises a plurality of valve attachment features, which are configured to releasably attach to corresponding features on the frame a prosthetic heart valve. The inner surface of the lid can also comprise a lid attachment mechanism, which is configured to releasably attach to corresponding features on the jar. In FIGS. 7, 8 and 10, only the outer frame 16 of the prosthetic heart valve 10 is shown and the other components of the prosthetic heart valve are omitted for purposes of illustrating the attachment between the outer frame 16 and the lid 208.

Figure 9A:
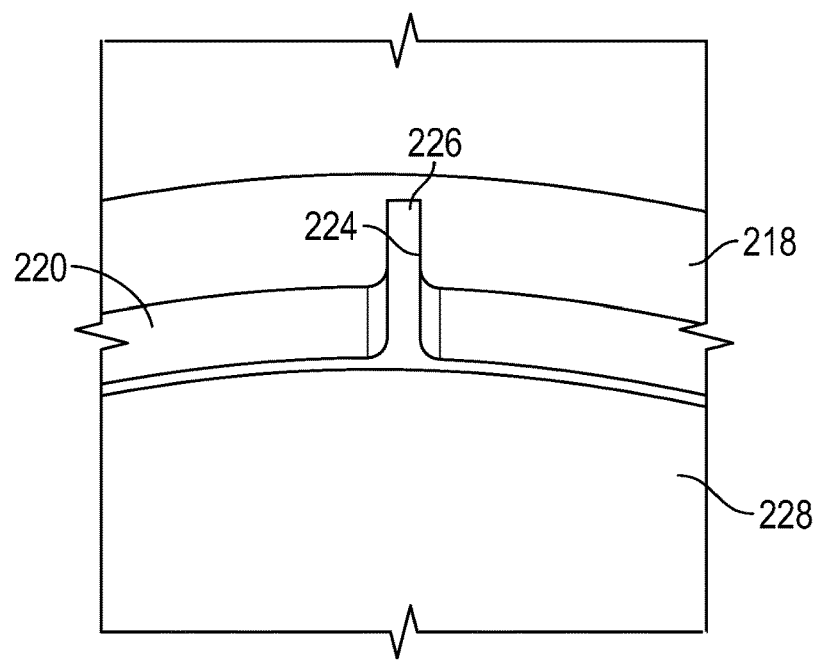
FIG. 9A is an enlarged view of a portion of the lid shown in FIG. 9.

As best shown in FIGS. 9 and 9A, an inner surface 216 of the upper portion 212 comprises a valve securement mechanism in the form of an annular projection or ring 218 (also referred to as an annular lip) having an inner peripheral edge 220 and an outer peripheral edge 222. The annular ring 218 can be formed with a plurality of valve attachment features in the form of a plurality of slots or notches 224 that are configured to receive the outer posts 38 of the outer frame 16 of the prosthetic heart valve 10. The notches 224 are circumferentially spaced from each other along an imaginary circle coincident with a circumference of the inner peripheral edge 220 of the annular ring 218. Each notch 224 can extend in a radial direction from the inner peripheral edge 220 partially through the ring 218 and can have a closed end 226 spaced inwardly from the outer peripheral edge 222. The inner peripheral edge 220 and the notches 224 can be slightly spaced from a central inner surface portion 228 of the lid to form a receiving space that accommodates tip portions of the outer posts 38, as further described below.

In alternative embodiments, the notches 224 can extend completely through the annular ring 218 from the inner peripheral edge 220 to the outer peripheral edge 222. In other embodiments, the notches 224 can extend from the outer peripheral edge 222 (i.e., the notches are open at the outer peripheral edge) partially through the annular ring 218 and have closed ends that are spaced from the inner peripheral edge 220.

The annular ring 218 in the illustrated embodiment is circular in shape, but it is to be understood that the ring may have other shapes, such as elliptical, D-shaped, or any other shape sufficient to accommodate the shape of the outer frame 16.

FIG. 10 shows the outer posts 38 disposed in the notches 224, which is effective to securely hold the prosthetic heart valve 10 relative to the lid 208. To attach the outer frame 16 to the lid 208, the outer posts 38 and/or the outflow end of the prosthetic heart valve 10 can be compressed or pinched a sufficient amount to allow the outer posts 38 to be inserted inside of the annular ring 218. Each outer post 36 can be aligned with a corresponding notch 224, after which the compression force on the outer posts 38 can be released to allow the posts to slide into the notches under the resiliency of the frame. Tip portions 58 of the outer posts 38 can be located in the space between the annular ring 218 and the adjacent surface portion 228 of the inner surface of the lid. The tip portions 58 have a width that is greater than the width of the notches 224, which prevents the prosthetic heart valve 10 from being pulled away from the lid in an axial direction while the outer posts 38 are positioned in the notches 224. Removal of the outer posts 38 from the notches 224 can be accomplished by compressing the prosthetic heart valve or just the inlet end of the prosthetic heart valve a sufficient amount to move the outer posts 38 radially inwardly until they are removed from the notches. Thereafter, the prosthetic heart valve 10 can be separated from the lid.

While the illustrated embodiment shows the outer posts 38 of the outer frame 16 secured within the notches 224, it should be noted that other components of the prosthetic heart valve can be secured within the notches. For example, in some embodiments, both the outer posts 38 of the outer frame 16 and the inner posts 38 of the inner frame 15 can be secured within the notches 224. In other embodiments, only the inner posts 38 of the inner frame 15 can be secured within the notches 224.

In some embodiments, the annular ring 218 and the notches 224 are sized such that the outer frame 16 (and the prosthetic heart valve) is not held in a state of compression once the outer posts 38 are placed within the notches 224. That is, after aligning the outer posts 38 with the notches 224 and releasing the compression force on the frame, the end of the outer frame 16 with the outer posts 38 can fully expand and the outer posts 38 are retained within the notches by the engagement of the tip portions 58 with the annular ring 218.

In other embodiments, the annular ring 218 and the notches 224 can be sized and/or shaped to retain the outer frame 16 (and the prosthetic heart valve 10) in a compressed or partially compressed state. The amount of compression under which the outer frame 16 (and the prosthetic heart valve 10) is retained can vary depending on the diameter of an imaginary circle coincident with the close ends 226 of the notches 224. Thus, when the outer posts 38 are placed within the notches 224, the outer posts 38 can expand radially outwardly to contact the closed ends 226, but prevent the posts from fully expanding, effectively retaining that end of the frame in a partially compressed state. The outer posts 38 therefore can exert an outward bias against the closed ends 226, which assists in retaining the posts within the notches and further increases the attachment force between the frame and the lid.

When the frame is formed from a self-expandable material (e.g., Nitinol), the inherent resiliency of the frame causes the outer posts 38 to expand within the notches 224. If the frame is formed from a plastically-expandable material (e.g., stainless steel), the outer posts 38 can still exhibit sufficient resiliency to self-expand after being compressed and then released within the notches 224 if the posts are not initially compressed to such an extent that causes plastic deformation of the outer posts 38. Thus, it should be understood that the lid 208 can be used to retain self-expanding frames and plastically-expandable frames. Although less desirable, in some embodiments, the frame can undergo at least some amount of plastic deformation when placing the outer posts 38 within the notches 224 and then re-expanded via an outside force (e.g., a manual force applied to the frame or the posts).

With continued reference to FIG. 9, the inner surface of the side wall 214 of the lid 208 may further comprise a storage jar attachment region 230. The storage jar attachment region may contain one or more storage jar attachment features configured to releasably attach to corresponding features on the exterior of the upper end portion of the wall 206 of the storage jar 202. In some embodiments, as illustrated in FIG. 9, the one or more storage jar attachment features may include helical threads 232 (also referred to as screw threads), which configured to engage with corresponding helical threads 232 on the upper end portion of the wall 206 of the storage jar 202.

Figure 11:
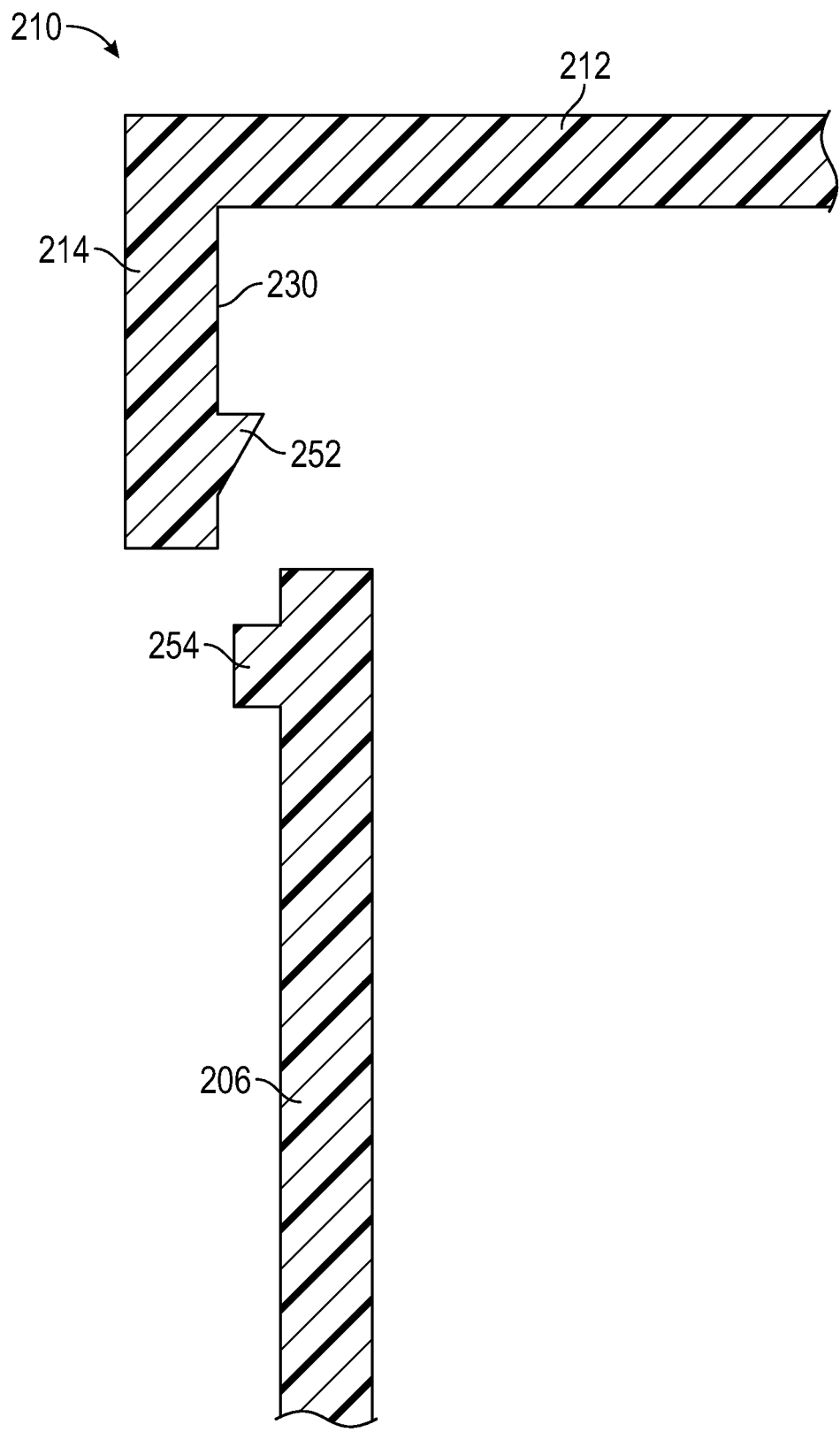
FIG. 11 is a schematic depiction of an alternative mechanism for attaching the lid and the jar to each other.

While FIGS. 9 and 10 depict a lid configured to attach to a jar with helical threads, other storage jar attachment mechanisms can be used. For example, as illustrated in FIG. 11, the one or more jar attachment features disposed on jar attachment region 230 may comprise one or more features for forming a press-fit or snap-fit connection with the jar. For example, the jar attachment region 230 of the lid can comprise an annular ridge 252, and the upper end portion of the jar side wall 206 can comprise an annular lip 254 on the exterior of jar 202. The ridge 252 is configured to releasably engage with lip 254 when lid 208 is pressed onto the upper end portion of the jar side wall 206 202. While the embodiment illustrated in FIG. 11 shows a ridge 252 with a generally triangular or sloped cross-section and a lip 254 with a generally rectangular cross-section, it is to be understood that the geometries of the ridge and the lip may have other configurations, such as a rectangular ridge 252 and a triangular or sloped lip 254, a configuration wherein one or both of the ridge and the lip have a cross-section that is a segment of a cylinder or sphere, or any other geometries suitable for a releasable engagement between the ridge and the lip.

FIG. 6 shows the fully assembled storage jar assembly 200 with the prosthetic heart valve 10 attached to the lid 208 and the lid 208 attached to the jar 202. During assembly (such as at the manufacturing site of the prosthetic heart valve), the assembler can attach the prosthetic heart valve 10 to the lid 208 as previously described, fill the jar with a hydrating solution (e.g., glutaraldehyde), and then place the lid on top of the jar and secure it place (e.g., by screwing the lid onto the jar). Desirably, a sufficient volume of hydrating solution is placed in the jar so as to fully immerse the leaflets 50 of the prosthetic heart valve.

In some embodiments, the leaflets 50 can be made of a material or chemically treated such that they can be stored without a hydrating solution within the jar. In such embodiments, the storage jar assembly 200 can comprise a prosthetic heart valve (e.g., prosthetic heart valve 10) attached to the lid 208 and stored inside the jar 202, which can be free of any liquids except for any moisture retained by the leaflets following a tissue treatment process. Methods for treating tissue leaflets for so-called dry storage are disclosed in U.S. Pat. No. 8,007,992 and U.S. Patent Publication No. 2009/0164005, filed Dec. 18, 2008, both of which documents are incorporated herein by reference.

In the fully assembled state, the assembly 200 can be shipped to end users (e.g., hospitals) and stored until the prosthetic heart valve is used in a heart valve replacement procedure. Prior to implantation, the user (e.g., a physician) can remove the lid from the jar and then remove the prosthetic heart valve from the lid, as previously described. Advantageously, the lid 208 securely retains the prosthetic heart valve in place relative to the lid to prevent or minimize damage to the prosthetic heart valve during shipping and storage. Further, removal of the prosthetic heart valve from the jar and the lid is relatively simple and easy compared to known storage assemblies, does not require any special tools, and avoids or minimizes contact and possible damage to the leaflets 50.

In alternative embodiments of the storage jar assembly disclosed herein, the lid may further comprise a valve holder or valve securement mechanism that is spaced below the side wall of the lid to position the prosthetic heart valve closer to the bottom of the jar. This may be done, for example, to enable a prosthetic heart valve to be fully-immersed in a hydrating fluid when stored inside the jar (or to fully immerse the prosthetic heart valve using a relatively smaller volume of a hydrating fluid, or to facilitate detachment of the prosthetic heart valve from the lid of the storage jar assembly). In these alternative embodiments, the prosthetic heart valve may be stored in a partially compressed state as previously described.

Figure 12:
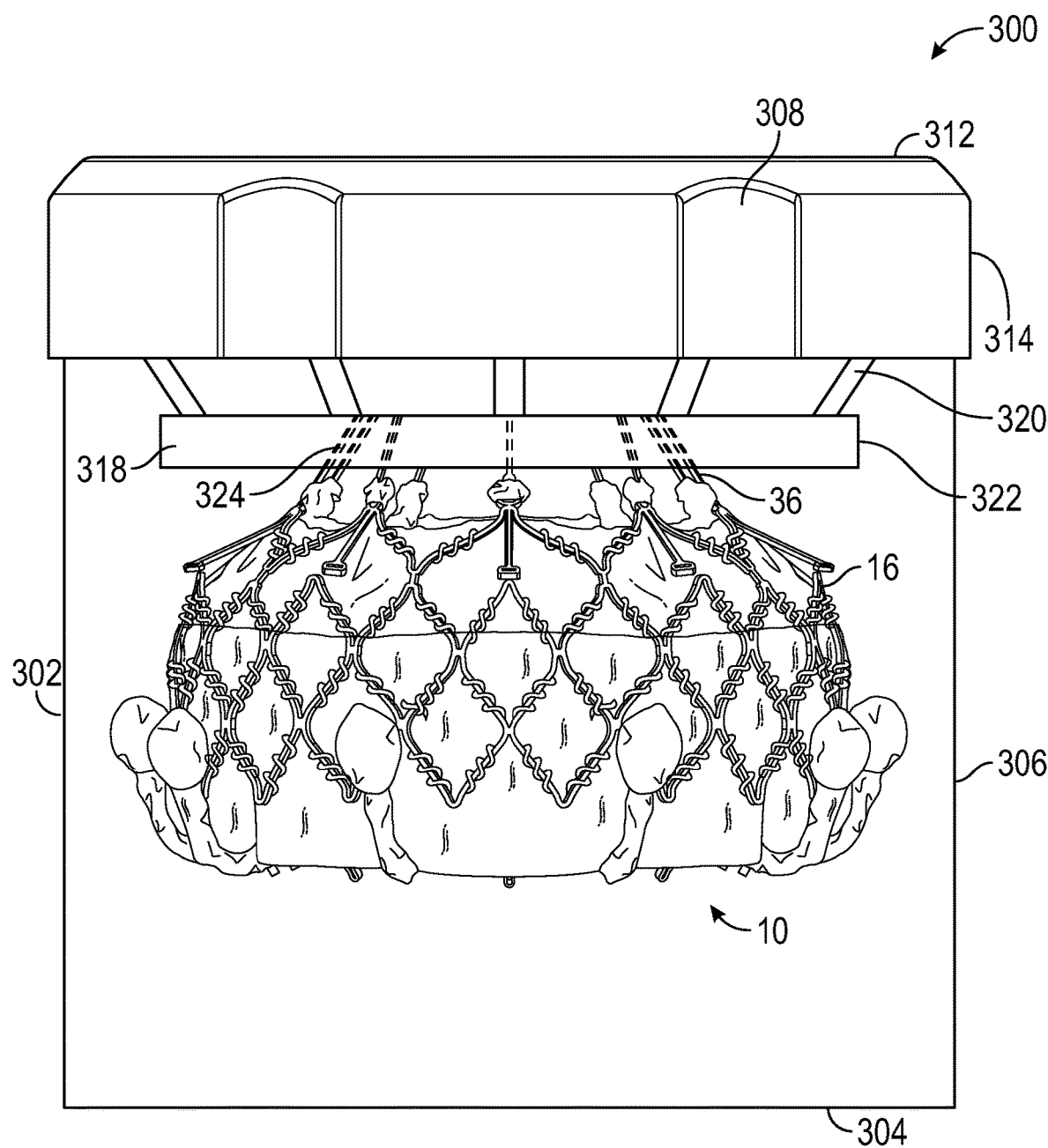
FIG. 12 is a side elevation view of an alternative embodiment of a storage jar assembly.

In an exemplary embodiment shown in FIG. 12, a storage jar assembly 300 can comprise a jar 302 and a lid 308. The jar 302 comprises a base 304 and a wall 306 defining an opening for the jar at an upper end thereof. The jar 302 can have the same configuration and features as described above for the jar 202 and therefore is not described further. The lid 308 can comprise an upper portion 312 and a side wall 314. The lid 308 can have the same configuration as the lid 308 described above except that it includes a securement mechanism for a prosthetic heart valve that is offset from the inner surface of the lid, and more specifically, spaced below a side wall 314 of the lid 308.

Although the following description of the storage jar assembly 300 proceeds with reference to the prosthetic heart valve 10, it should be understood that other prosthetic heart valves (e.g., prosthetic heart valve 100 or any of those disclosed in Publication Nos. US2016/0317301, US 2018/0055629 and US 2019/0262129, and U.S. Pat. No. 10,350,062) can be used with the storage jar assembly 300.

The valve securement mechanism (also referred to as an "attachment structure") can comprise an annular ring 318 and one or more struts or posts 320. Similar to the annular ring 218, the ring 318 can be configured to be releasably attachable to the prosthetic heart valve 10. The annular lip 318 can have a thickness in the radial direction defined by an inner peripheral edge (not visible in FIG. 12) and an outer peripheral edge. Each of the one or more struts 320 has a lower end connected to the annular ring 318 and an upper end connected to an inner surface of the lid 308.

With continued reference to FIG. 12, the annular ring 318 may further comprise a plurality of valve attachment features in the form of notches 324. In some embodiments, as shown in FIG. 12, the notches 324 can extend from the inner peripheral edge of annular ring 318 partially through the annular ring, similar to the notches 224 shown in FIGS. 9 and 9A. In other alternative embodiments, the notches 324 can extend completely through the annular ring 318 from its inner peripheral edge to its outer peripheral edge 322. In other embodiments, the notches 324 can extend from the outer peripheral edge 322 partially through the annular ring 318. Similar to the notches 224, the notches 324 are configured to releasably attach to corresponding features of the prosthetic heart valve 10. For example, the notches 324 can be configured to receive the outer posts 38 of the outer frame 16 as shown, the inner posts 38 of the inner frame 15, the outer posts 38 and the inner posts 38, or other components of the frame assembly 12.

The prosthetic heart valve 10 can be attached to and removed from the annular ring 318 of the lid 308 in the same manner as described for the embodiment of FIGS. 6-10. Moreover, the annular ring 318 and the notches 324 can be configured to retain the prosthetic heart valve 10 in a fully expanded state, or in a partially compressed state, as previously described for the embodiment of FIGS. 6-10. As shown in FIG. 12, when the storage jar assembly 300 is in the fully assembled state with the prosthetic heart valve 10 attached to the annular ring 318 and the lid 308 is attached to the jar, the prosthetic heart valve is held closer to the bottom of the jar and is spaced from the side wall 314 of the lid. This can allow the prosthetic heart valve 10 to be fully immersed in a hydrating fluid using a relatively smaller volume of fluid as compared to the embodiment of FIG. 6. Also, by holding the prosthetic heart valve 10 outside of the space defined by the side wall 314 of the lid, it may be relatively easier to remove the prosthetic heart valve from the annular ring.

Figure 13:
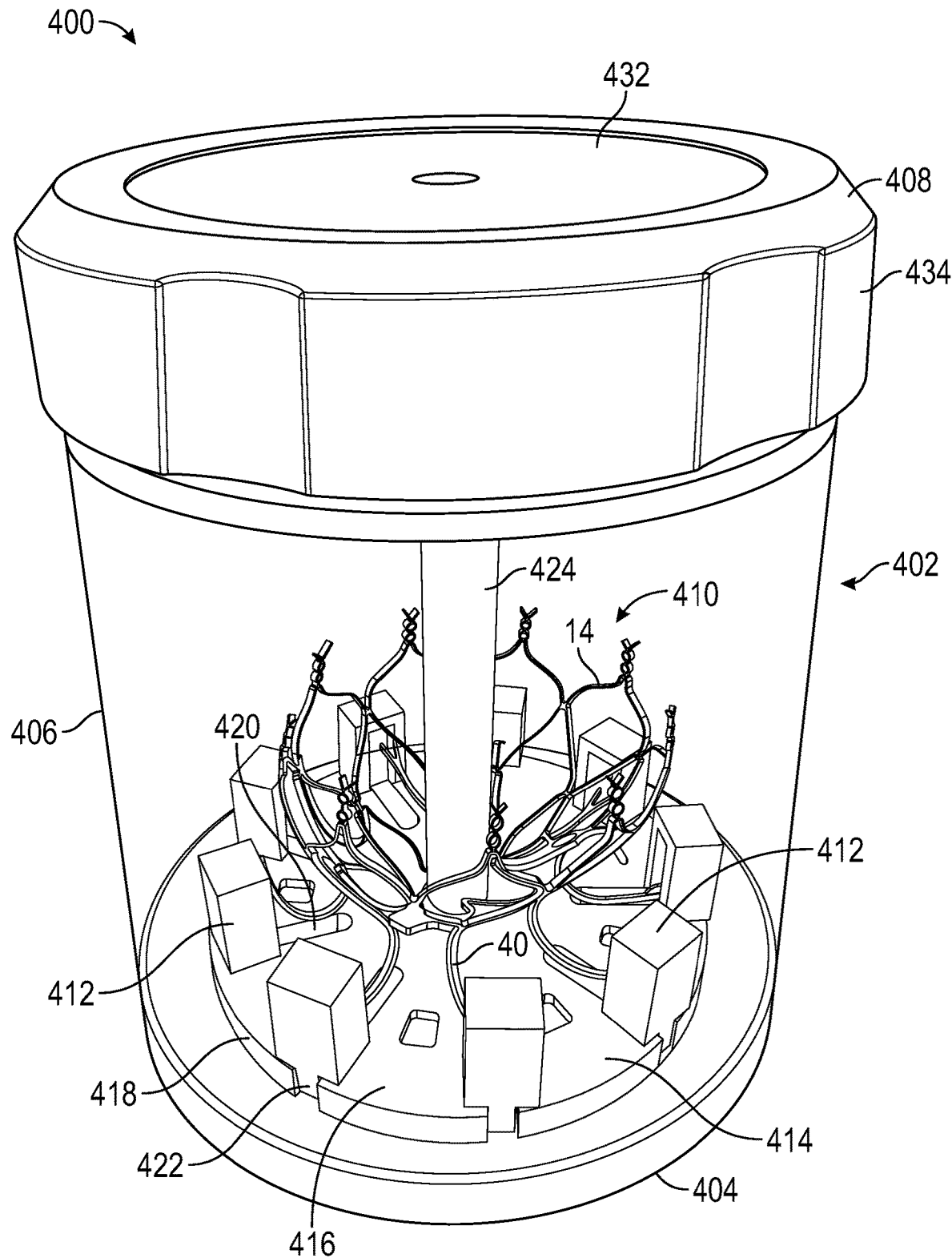
FIG. 13 is a perspective view of a storage jar assembly having a valve holder, according to another embodiment.

Referring now to FIG. 13, a storage jar assembly 400 according to another embodiment is shown. The storage jar assembly 400 includes a jar 402. The jar 402 generally comprises a base 404 and an upstanding side wall 406 extending upwardly from the base 404. The upper end portion of the wall 406 can form a mouth defining an opening at the upper end of the jar 402. The jar 402 can be configured to receive a prosthetic heart valve, such as prosthetic heart valve 10. The storage jar assembly can also include a lid 408, configured to releasably attach to the jar 402. Although the following description of the storage jar assembly 400 proceeds with reference to the prosthetic heart valve 10, it should be understood that other prosthetic heart valves, (e.g., prosthetic heart valve 100 or any of those discussed in Publication Nos. US2016/0317301, US2018/0055629 and US2019/0262129, and U.S. Pat. No. 10,350,062) can be used with the storage jar assembly 400.

Figure 14:
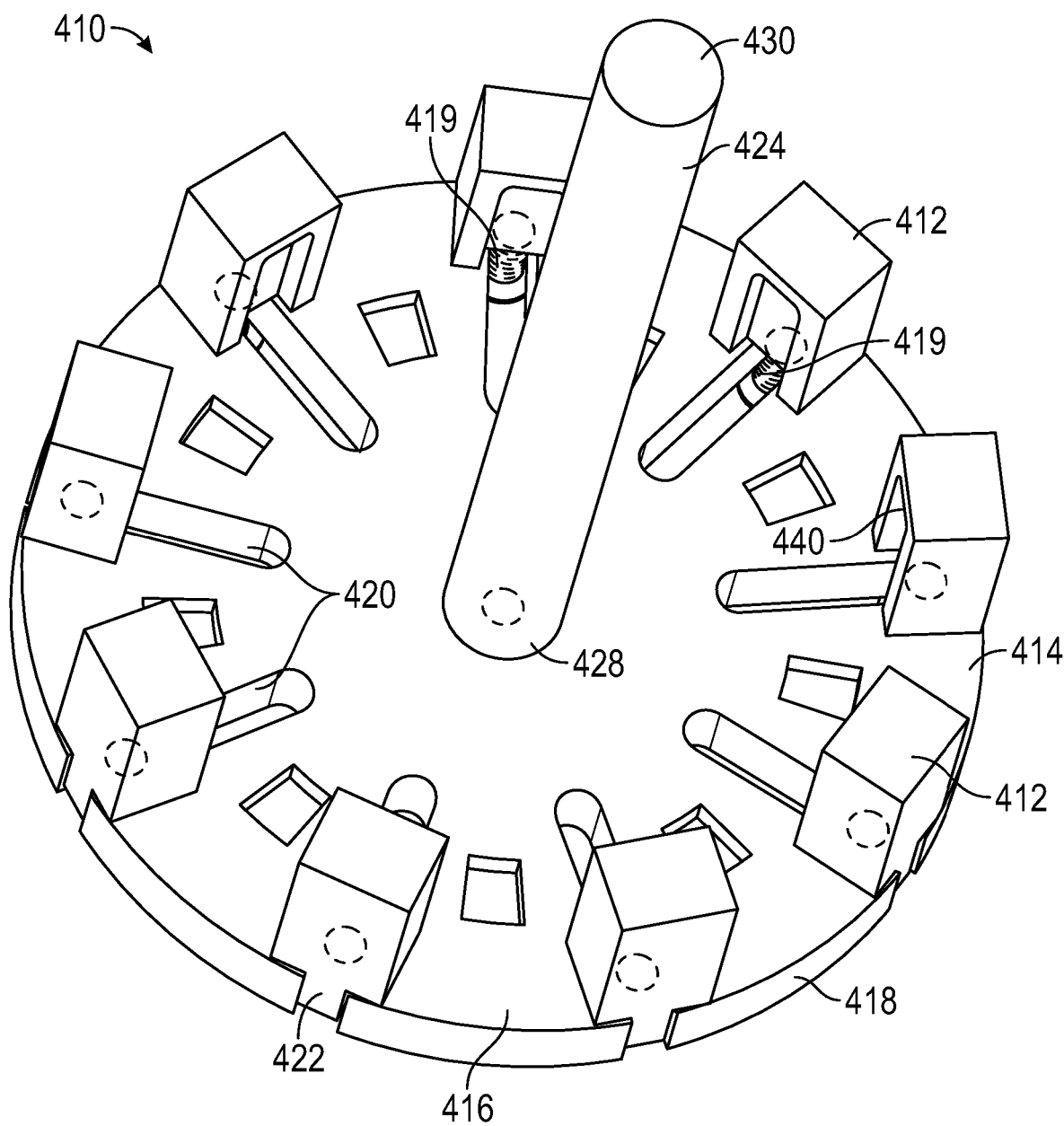
FIG. 14 is a perspective view of the valve holder depicted in FIG. 13.
Figure 15:
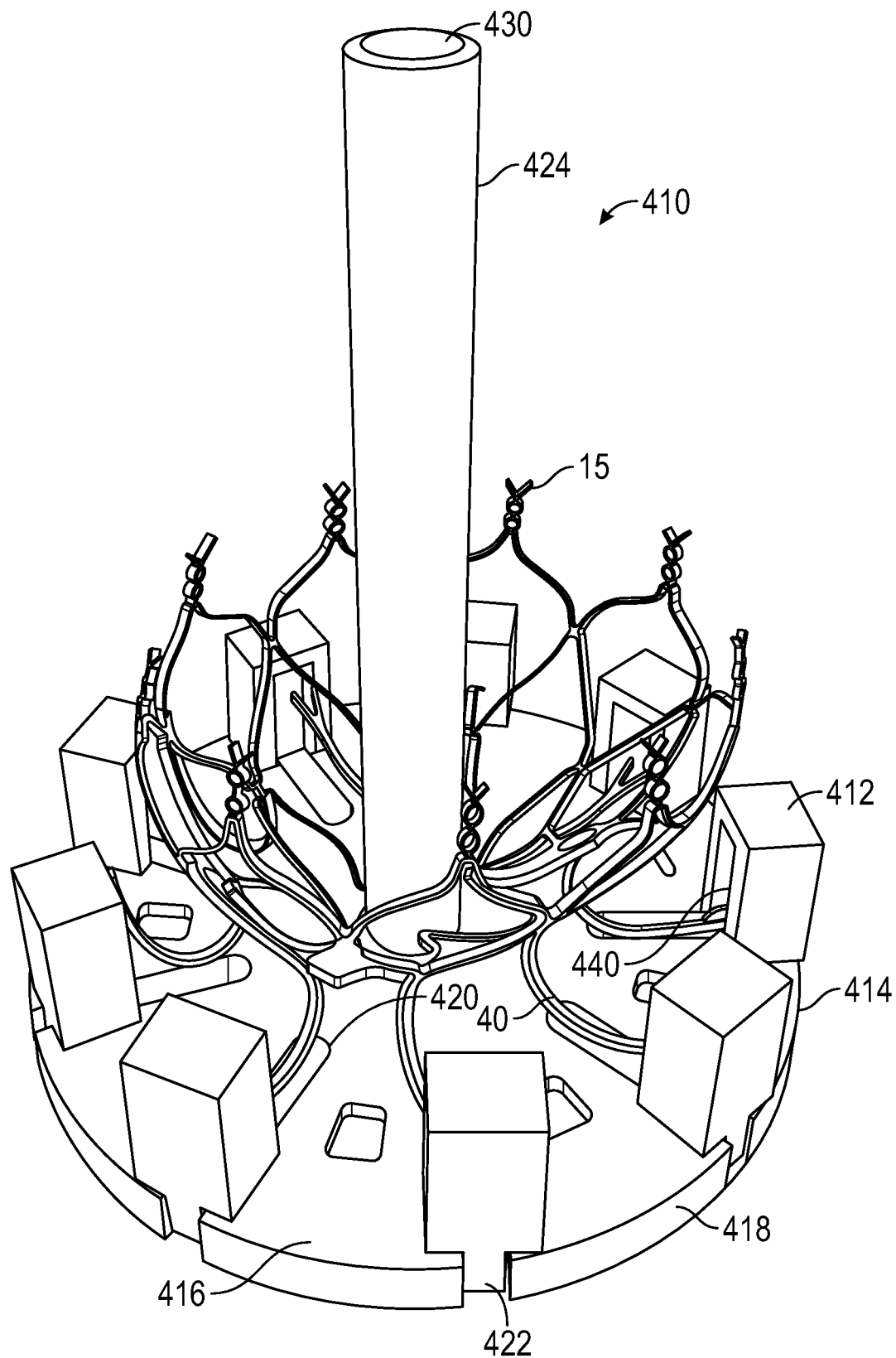
FIG. 15 is a perspective view of the valve holder depicted in FIG. 14 showing a representative outer frame of a prosthetic heart valve disposed within the valve holder.

The storage jar assembly 400 may also have a valve securement mechanism or valve holder 410 that can be configured to be received by the jar 402 and to receive the prosthetic heart valve 10 or the frame assembly 12 of the prosthetic heart valve 10. The valve holder 410 may be configured to hold the prosthetic heart valve 10 and/or the frame assembly 12 in a compressed or partially compressed state. As shown in FIGS. 13-15, in some embodiments, the valve holder 410 can have a plurality of valve retention members 412 and a base 414. In FIGS. 13 and 15, only the inner frame 15 of the prosthetic heart valve 10 is shown, and the other components of the prosthetic heart valve are omitted for the purpose of illustrating the interaction of the valve holder 410 and the inner frame 15 of the prosthetic heart valve 10.

In some embodiments, the base 414 has a circular cross-sectional profile as shown. The base 414 has an upper surface 416, a lower surface 417, and an outer peripheral edge 418 extending between the upper surface 416 and the lower surface 417. The diameter of the base 414 can be less than the diameter of the opening defined by the mouth at the upper end of the jar 402 and allow for the valve holder 410 to pass through the mouth at the upper end of the jar 402 as the valve holder is inserted into or removed from the jar. While the base 414 illustrated in FIGS. 13-15 is shown as having a circular cross-sectional profile, it is to be understood that base 414 may, in some embodiments, have a square cross-section, a hexagonal-cross section, a D-shaped cross-section, or any cross-section suitable for receiving the inner frame 15 of prosthetic heart valve 10.

Referring to FIGS. 13-15, the valve holder 410 may also have a plurality of valve retention members 412. The valve retention members 412 may be disposed on the upper surface 416 of the base 414 of the valve holder 410. In some embodiments, the valve retention members 412 may be positioned along the outer peripheral edge 418 of the base 414 of the valve holder 410. In alternative embodiments, valve retention members 412 may be inset from the outer peripheral edge 418 of the base 414 towards the center of the base.

In some embodiments, the positioning of valve retention members 412 relative to the outer peripheral edge 418 and the center of the base 414 of the valve holder 410 may be adjustable. In one embodiment best illustrated in FIG. 14, the base 414 further comprises a plurality of slots 420 angularly spaced from one another and extending from the outer peripheral edge 418 of the base 414 towards the center of the base, and each valve retention member 412 further comprises a projection 422. The slots 420 on the base 414 may be configured to receive the projections 422 of the valve retention members 412 and to permit the positioning of valve retention members 412 to be adjustable by sliding the projections 422 along the length of the slots 420. While FIG. 14 depicts the slots 420 disposed on the base 414 and the projections 422 disposed on the valve retention members 412, it is to be appreciated that in alternative embodiments, the projections might be disposed on the base 414 and the slots might be disposed on the valve retention members 412.

The valve retention members 412 can be secured to the base 414 by a plurality of fasteners, such as the illustrated screws 419. Each screw 419 can extend through a corresponding slot 420 and into a corresponding threaded bore in a valve retention member 412. Loosening the screws 419 allows the valve retention members 412 to be slid radially inwardly and outwardly along the upper surface of the base 414. Tightening the screws 419 fixes the positions of the valve retention members 412 relative to the base 414. The positions of the valve retention members 412 can be adjusted to adjust the amount of retention force that is applied to the prosthetic heart valve 10, as further described below, and/or accommodate prosthetic heart valves of different sizes.

Figure 16:
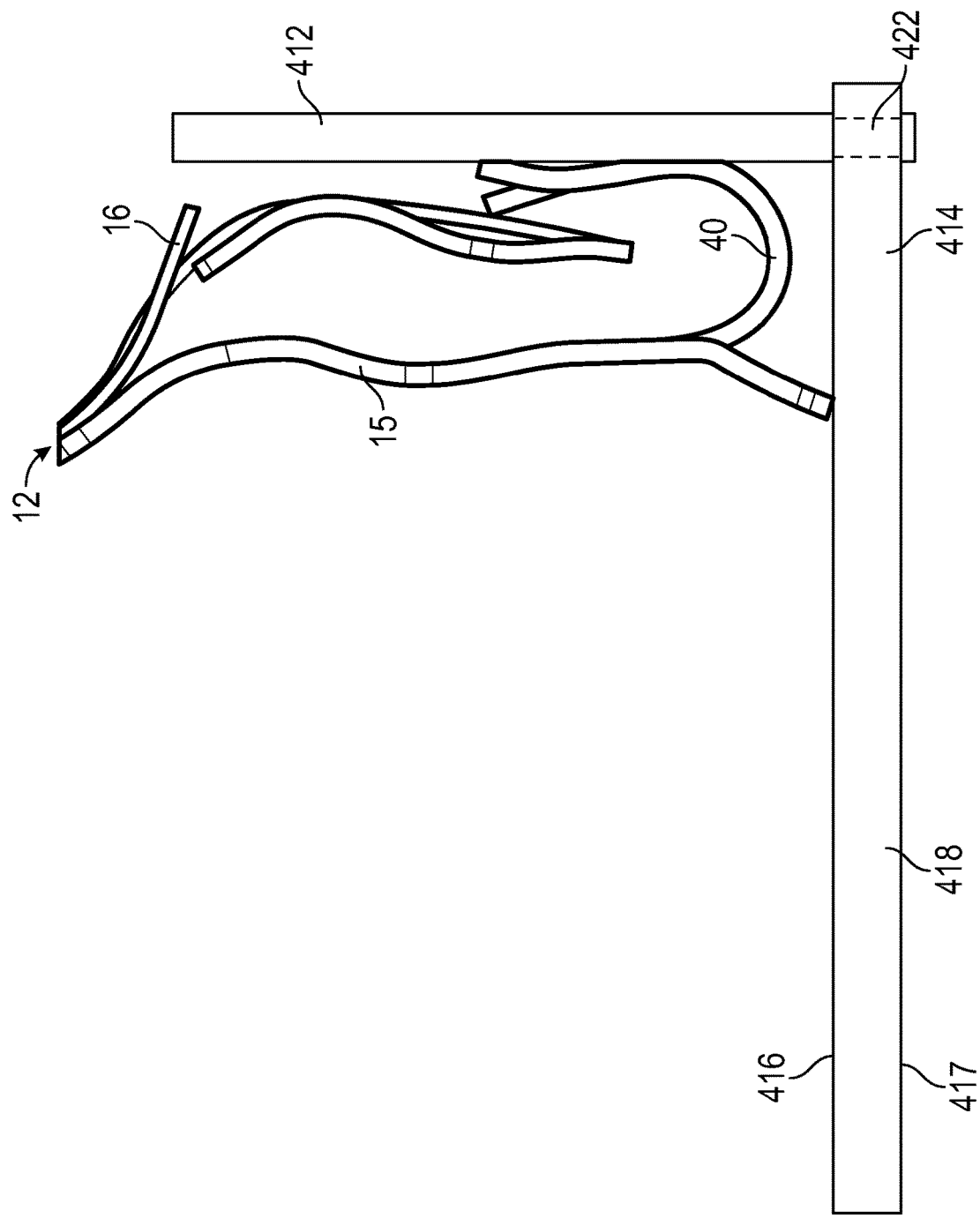
FIG. 16 is a schematic side view of a valve retention member of the valve holder of FIGS. 13-15 shown in contact with struts of a representative outer frame of a prosthetic heart valve.

The valve retention members 412 may be configured to contact a corresponding inner frame anchoring feature 40 of the inner frame 15 of prosthetic heart valve 10. As best illustrated in FIG. 16, the valve retention members 412 may be configured to hold the frame assembly 12 (and thus the prosthetic heart valve 10) in a compressed or partially compressed state. The degree of compression imparted on the prosthetic heart valve 10 may be determined by the positioning of the valve retention members 412 relative to the outer peripheral edge 418 of the base 414. In the illustrated embodiment, the contact between the valve retention members 412 and the inner frame anchoring features 40 pushes the inner frame anchoring features 40 towards the center of the base 414 and against the outer frame 16. In this fashion, both the inner frame 15 and outer frame 16, and therefore the entire frame assembly 12 of prosthetic heart valve 10 are at least partially compressed by the valve retention members 412. In other embodiments, the amount of compression can be selected to partially compress the tip portions of the anchoring features, but otherwise may not cause any corresponding compression of the outer frame 16.

While FIGS. 13, 15, and 16 show valve retention members 412 configured to contact corresponding inner frame anchoring features 40 of prosthetic heart valve 10, it is to be understood that in other embodiments, the valve retention members 412 can be configured to contact other portions of the frame assembly, such as the outer frame body 26, the anchoring features 28 of the outer frame 16, and/or the inner frame body 24.

The compressive strain imparted on the frame assembly 12 desirably is great enough that the outermost diameter of the prosthetic heart valve 10 is less than the inner diameter of the jar 402 (to allow the prosthetic heart valve to be easily inserted into and removed from the jar), and small enough that the prosthetic heart valve 10 may be kept under the imparted strain for the entire storage life of the prosthetic heart valve 10 without damaging the frame assembly or other components of the prosthetic heart valve. In particular embodiments, the compressive strain can be less than 6%, such as 3% or less or 1% or less.

In certain alternative embodiments, valve retention members can be configured to contact the corresponding inner frame anchoring feature 40 or other portions of the frame assembly without imparting a compressive strain to the frame assembly 12 while still retaining the prosthetic heart valve relative to the valve holder during shipping and storage. For example, in some embodiments, each valve retention member 412 can include a recessed portion 440 on the inner radially facing surface of the valve retention member 412. Each recessed portion 440 can receive a respective anchoring feature 40 or another portion of the frame assembly. When the prosthetic heart valve is positioned on the valve holder 410, the anchoring features 40 can be aligned with and at least partially inserted into the recessed portions 440 (see FIG. 15). Moreover, in lieu of or in addition to the recessed portions 440, portions of the anchoring features 40 can be positioned within the slots 420 (see FIG. 15). In some embodiments, the positioning of the anchoring features 40 in the recessed portions 440 and/or the slots 420 can retain the prosthetic heart valve relative to the valve holder without imparting any compressive stain on the frame assembly.

When the frame assembly 12 is formed from a self-expandable material (e.g., Nitinol), the inherent resilience of the frame causes the inner frame anchoring features 40 to press against the valve retention members 412 to cause the compressive strain on the prosthetic heart valve. If the frame is formed from plastically-expandable material (e.g., stainless steel, polymer), the inner frame anchoring features 40 can still exhibit sufficient resiliency to self-expand after being compressed and released within the valve holder 410, if the frame is not initially compressed to such an extent that causes plastic deformation of the anchoring features 40 or other components of the frame assembly. Thus, it should be understood that the valve holder 410 can be used to retain self-expanding frames and plastically-expandable frames. Although less desirable, in some embodiments the anchoring features 40 and/or other components of the frame assembly can undergo at least some amount of plastic deformation when retained by valve retention members 412, and then be re-expanded via an outside force (e.g., a manual force applied to the frame or the anchoring features).

As shown in FIGS. 13-15, the valve holder 410 may also have a column or shaft 424. The column 424 has a lower end portion 428 and an upper end portion 430. The lower end portion 428 may contact or be connected to the upper surface 416 of the base 414 of the valve holder 410. The column 424 may project away from the base 414 of the valve holder 410 in an axial direction such that, when the valve holder 410 is within the jar 402, the column 424 extends towards the mouth of the jar 402, as best illustrated in FIG. 13. While FIGS. 13-15 show the column 424 positioned at the center of the base 414, it is to be understood that, in some embodiments, the column 424 may be positioned at a different location on the base 414, such as between the peripheral edge 418 and the center of the base, or at the peripheral edge 418.

In certain embodiments, the column 424 may extend such that, when the valve holder 410 is within the jar 402, the upper end portion 430 of the column 424 may be placed at or near the mouth of the jar 402, as best seen in FIG. 13. In some embodiments, the upper end portion 430 of the column 424 is configured to come into contact with an inner surface of the lid 408 when the valve holder 410 is within the jar 402 and the lid 408 is attached to the jar 402. It is to be appreciated that these embodiments offer several advantages, such as facilitating the removal of the valve holder 410 from the jar 402 by a user or providing additional stability to the valve holder 410 during storage and transport of the storage jar assembly.

In some embodiments, best illustrated in FIG. 15, the column 424 can be configured to pass through the center of the frame assembly 12 of the prosthetic heart valve 10, such as through the center of the inner frame 15 and/or the outer frame 16 when the prosthetic heart valve is received by valve holder 410. However, it is to be understood that, in alternative embodiments, the column 424 may not pass through the center or any other portion of the frames 15, 16 of the prosthetic heart valve 10.

In some embodiments, as illustrated in FIG. 14, the column 424 can be cylindrical with a uniform circular cross-section. However, it is to be understood that column may have alternative geometries, such as a cross-section that varies along its length, or the column may have a different cross-sectional shape such as a square cross-section, a hexagonal cross-section, a D-shaped cross-section, or any other cross-section suitable for passing through the frames 15, 16 of the prosthetic heart valve 10 and/or facilitating the removal of the valve holder 410 from the jar 402.

Returning to FIG. 13, the storage jar assembly 400 may further include a lid 408 that can have an upper portion 432 and a downwardly depending side wall 434. The inner surface of the lid 408 can further comprise a storage jar attachment mechanism, which is configured to releasably attach to corresponding features on the jar 402. It is to be understood that the storage jar attachment mechanism of lid 408 may include any of the storage attachment features previously described, such as helical threads, screw threads, press-fit, or snap-fit attachment features.

In some embodiments, an inner surface of the upper portion 432 of the lid 408 may further comprise a column securing feature configured to receive upper end portion 430 of column 424 when the valve holder 410 is within the jar 402 and the lid 408 is attached to the jar 402. The column securing feature may be, for example, a recess or indent formed in the inner surface of the upper portion 432 with a geometry suitable for receiving the upper end 430 of a corresponding column 424.

In some embodiments, the upper end portion 430 of the column 424 can be connected to the upper portion 432 of the lid 408, which allows the valve holder 410 and a prosthetic heart valve 10 retained by the valve holder to be inserted into and removed from the jar 402 by manipulating the lid 408. In some embodiments, the upper end portion 430 of the column can be removably attached to the lid 408. This allows the valve holder to be disconnected from the lid after removing the valve holder and the prosthetic heart valve from the jar, which can facilitate removal of the prosthetic heart valve from the valve holder.

FIG. 13 shows the fully-assembled storage jar assembly 400, with the valve holder 410 placed within jar 402 and retaining the prosthetic heart valve 10. During assembly (such as at the manufacturing site of the prosthetic heart valve), the assembler can place the prosthetic heart valve 10 within the valve holder 410 as previously described, place the valve holder 410 and the prosthetic heart valve within jar 402, fill the jar with a hydrating solution (e.g., glutaraldehyde), place the lid on top of the jar, and then secure it in place (e.g., by screwing the lid onto the jar). Desirably, a sufficient volume of hydrating solution can be placed in the jar so as to fully immerse the leaflets 50 of the prosthetic heart valve.

In some embodiments, the leaflets 50 can be made of a material or chemically treated such that they can be stored without hydrating solution within the jar. In such embodiments, the storage jar assembly 400 can comprise a prosthetic heart valve held by valve holder 410 and stored within jar 402, which can be free of any liquids except for any moisture retained by the leaflets following a tissue treatment process. Methods for treating tissue leaflets for so-called dry storage are disclosed in U.S. Pat. No. 8,007,992 and U.S. Patent Publication No. 2009/0164005, filed Dec. 18, 2008, both of which documents are incorporated herein by reference.

In the fully assembled state, the storage jar assembly 400 can be shipped to end users (e.g., hospitals) and stored until the prosthetic heart valve is used in a heart valve replacement procedure. Prior to implementation, the user (e.g., a physician) can remove the lid from the jar, withdraw the valve holder from the jar, and then remove the prosthetic heart valve from the valve holder. The valve holder 410 securely retains the prosthetic heart valve 10 in place within the jar 402 to prevent or minimize damage to the prosthetic heart valve during shipping and storage. Further, the column 424 of the valve holder 410 facilitates the removal of the prosthetic heart valve 10 from the jar 402, as it is relatively easier to reach and grasp compared to known storage assemblies, does not require any specialized tools, and avoids or minimizes direct contact to the prosthetic heart valve 10, the leaflets 50, or the frame assembly 12.

Figure 17:
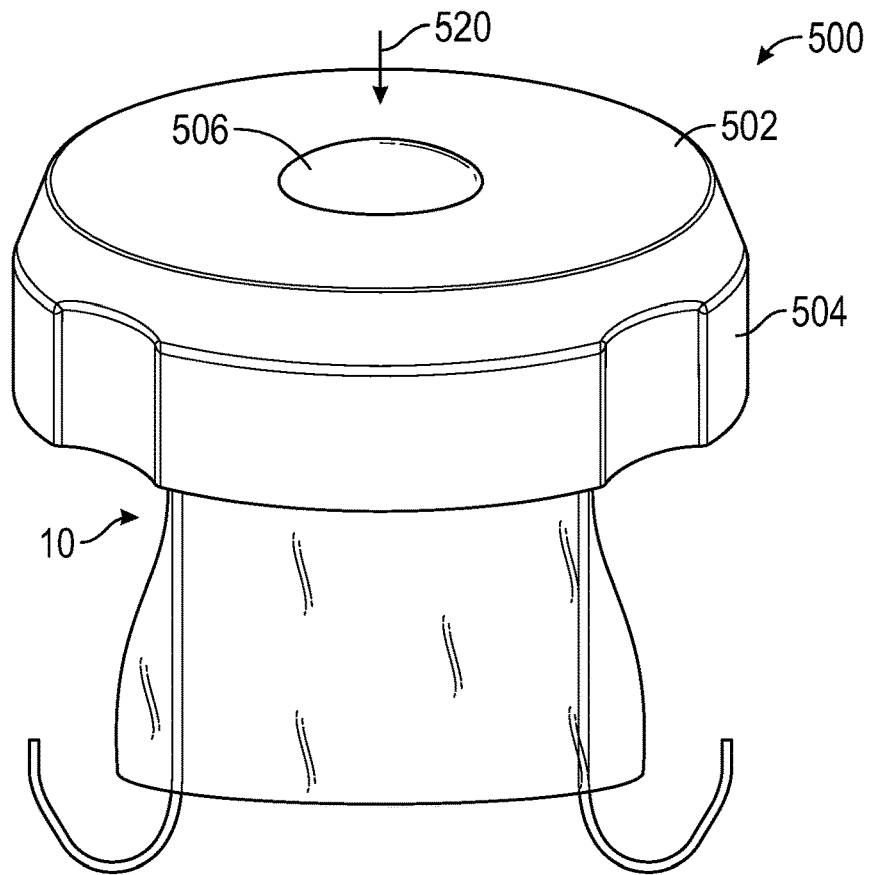
FIG. 17 is a perspective view of a lid for use with a storage jar assembly, having a valve release button, showing an exemplary prosthetic heart valve attached to the lid.
Figure 18:
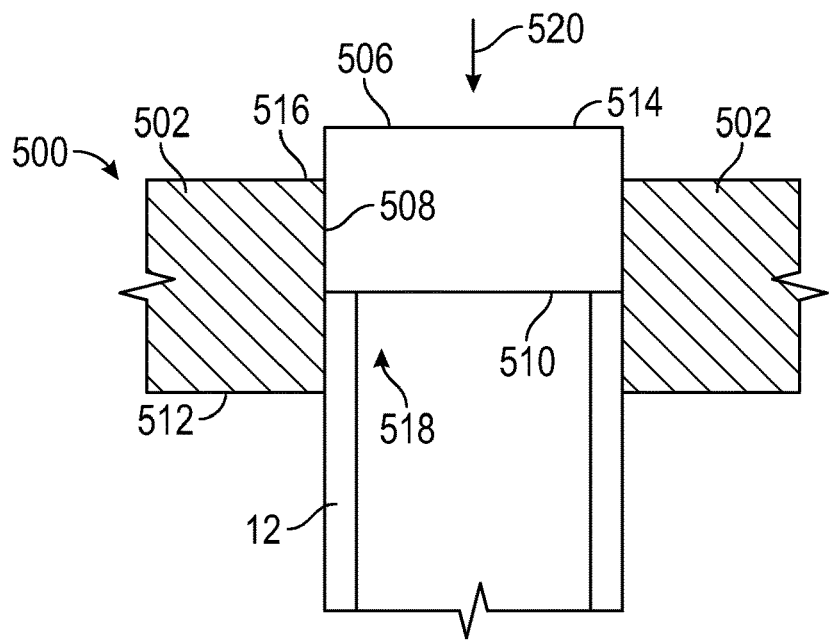
FIG. 18 is a cutaway schematic view of a portion the lid and a portion of the frame of the prosthetic heart valve of FIG. 17.

Referring now to FIGS. 17-18, a lid 500 for a storage jar assembly according to another embodiment is shown. The lid 500 can include an upper portion 502 and a downwardly depending wall 504. The lid 500 can be configured to receive a prosthetic heart valve such as prosthetic heart valve 10. The lid 500 can further be configured to releasably attach to a valve storage jar (not shown) configured to receive the prosthetic heart valve 10, such as the jars previously disclosed, to form a storage jar assembly. Although the following description of the lid 500 proceeds with reference to the prosthetic heart valve 10, it should be understood that other prosthetic heart valves (e.g., prosthetic heart valve 100 or any of those discussed in Publication Nos. US 2016/0317301, US2018/0055629 and US 2019/0262129, and U.S. Pat. No. 10,350,062) can be used with the lid 500.

As shown in FIG. 17, the lid 500 may further comprise a valve release mechanism, such as a button 506 disposed on and/or within the upper portion 502 of the lid. As best illustrated in FIG. 18, the button 506 may be formed from a separate body set within an opening of the upper portion 502 of lid 500, forming a lid-button interface 508. The button 506 may be configured to slidably engage with the upper portion 502 of lid 500 along the lid-button interface 508. The slidable engagement of button 506 and upper portion 502 may allow the button 506 a range of movement with relation to the upper portion having both an upper limit and a lower limit. In some embodiments, the lower limit of the movement range is defined at a point when a lower surface 510 of the button 506 is flush with or lower than a lower surface 512 of the upper portion 502, and the upper limit of the movement range is defined at a point where the lower surface 510 of the button 506 is above the lower surface 512 of the upper portion 502 and/or where an upper surface 514 of the button 506 is elevated above an upper surface 516 of the upper portion 502.

The button 506 and the upper portion 502 of the lid may further be configured such that they form the valve attachment feature 518 on the inner surface of the upper portion 502 of the lid 500, beneath the button 506. In some embodiments, best illustrated in FIG. 18, the valve attachment feature 518 is a circular recession defined by the lower surface 510 of the button 506 and the lid-button interface. The valve attachment feature 518 may be configured to receive corresponding features of a frame 12 of a prosthetic heart valve 10, such as the angularly spaced outer posts 36 shown in FIG. 1. In some embodiments, the diameter of attachment feature 518 may be configured to be less than the diameter defined by the angularly spaced outer posts 36 in a fully-expanded state. In this way, the compressive forces exerted on angularly outer spaced posts 36 may cause interference forces sufficient to retain the prosthetic heart valve 10 in the valve attachment feature.

While the valve attachment feature 518 has been described as a circular recession, it is to be understood that any feature geometry suitable for retaining the angularly spaced outer posts 36 or other portions of the frame 12 of the prosthetic heart valve 10 may be used, such as an annular recession or groove, a polygonal recession, or a plurality of notches or indentations formed in the inner surface 512 of the upper portion 502 and/or the lower surface 510 of the button 506. In one embodiment, for example, notches or recesses (similar to notches 224) sized for receiving the outer posts 38 or other portions of the frame can be formed on the lower surface 512 and/or an inner surface of the upper portion 502 at the interface 508, and the button 506 can be configured to push the frame downwardly relative to the lid to push the outer posts 36 out of the notches. In some embodiments, the button 506 can be shaped to push the outer posts 38 radially inwardly away from the interface 508 and out of the notches as the button 506 is pressed downwardly relative to the upper portion 502 of the lid. In other embodiments, the outer posts 38 or other portions of the frame can be retained against the inner surface of the upper portion 502 at the interface 508 by the radial outward expansion of those portions of the frame against the adjacent inner surface of the upper portion 502.

Returning to FIG. 17, the inner surface of the lid 500 can further comprise a storage jar attachment mechanism (not shown), which is disposed on depending wall 504 and configured to releasably attach to corresponding features on the jar (not shown in FIGS. 17-18). It is to be understood that the storage jar attachment mechanism of lid 500 may include any of the storage attachment features previously described, such as helical threads, screw threads, press-fit, or snap-fit attachment features.

During assembly of a jar assembly comprising, in part, the lid 500 (such as at the manufacturing site of the prosthetic heart valve), the assembler can attach the prosthetic heart valve 10 to the lid 500 as previously described, fill the jar with a hydrating solution (e.g., glutaraldehyde), and then place the lid on top of the jar and secure it place (e.g., by screwing the lid onto the jar). Desirably, a sufficient volume of hydrating solution is placed in the jar so as to fully immerse the leaflets 50 of the prosthetic heart valve.

In a fully-assembled storage state, partially illustrated in FIG. 17, the lid 500 may be configured such that corresponding features of the prosthetic heart valve 10, such as the angularly spaced outer posts 36 or other elements of the frame 12 rest within the valve attachment feature 518. The prosthetic heart valve 10 thus may depend from the lid 500 and be contained within the valve storage jar in the fully-assembled storage state. In possible embodiment, when a jar assembly including the lid 500 is in the fully-assembled storage state, the button 506 may be near the upper limit of movement relative to upper portion 502 of lid 500.

In the fully-assembled storage state, the storage jar assembly including the lid 500 can be shipped to end users (e.g., hospitals) and stored until the prosthetic heart valve is used in a heart valve replacement procedure. Prior to implementation, the user (e.g., a physician) can press the button 506, moving the button 506 downwards relative to both the upper portion 502 of the lid 500 and the prosthetic heart valve 10, in the direction of arrow 520 in FIG. 18, causing the frame 12 or the angularly spaced outer posts 36 of the prosthetic heart valve 10 to be pushed or ejected from the valve attachment feature 518. In some embodiments, the prosthetic heart valve can be released prior to removing the lid from the jar, which causes the prosthetic heart valve 10 to detach from the lid 500 and become submerged or partially submerged in the hydrating solution (e.g., glutaraldehyde). Thereafter, the user can remove the prosthetic heart valve from jar just prior to loading the prosthetic heart valve onto the delivery device.

In other embodiments, the lid 500 can be removed from the jar while the prosthetic heart valve is still attached to the lid, after which the user can push the button 506 to release the prosthetic heart valve from the lid. Advantageously, this configuration allows a user to detach the prosthetic heart valve from the lid 500 while minimizing direct contact with the prosthetic heart valve and without requiring any tools, thereby facilitating the removal of the prosthetic heart valve from the storage jar assembly, and preventing or minimizing damage to the prosthetic heart valve.

In some embodiments, the lid 500 can include a locking feature or locking element that prevents inadvertent movement of the button 506 during shipping, storage and handling of the assembly prior to intended removal of prosthetic heart valve from the lid. The locking feature can be moved between a locked position and an unlocked position. In the locked position, the locking feature can contact and resist movement of the button 506. In the unlocked position, the locking feature is removed from contact with the button 506 and allows it to pushed relative to the upper portion 502 in order to release the prosthetic heart valve from the lid.

In some embodiments, the lid 500 can include a biasing element, such as a spring (e.g., a coil spring), configured to resiliently bias the button 506 to its upper limit of travel. When releasing the prosthetic heart valve from the lid, the user can press the button downwardly against the bias of the biasing element.

General Considerations

For purposes of this description, certain aspects, advantages, and novel features of the embodiments of this disclosure are described herein. The described methods, systems, and apparatus should not be construed as limiting in any way. Instead, the present disclosure is directed toward all novel and non-obvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present, or problems be solved.

Features, integers, characteristics, compounds, chemical moieties, or groups described in conjunction with a particular aspect, embodiment or example of the disclosure are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The disclosure is not restricted to the details of any foregoing embodiments. The disclosure extends to any novel one, or any novel combination, of the features disclosed in this specification (including any accompanying claims, abstract, and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods, systems, and apparatus can be used in conjunction with other systems, methods, and apparatus.

As used herein, the terms "a," "an," and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A," "B," "C," "A and B," "A and C," "B and C," or "A, B, and C."

As used herein, the term "coupled" generally means physically coupled or linked and does not exclude the presence of intermediate elements between the coupled items absent specific contrary language.

Directions and other relative references (e.g., inner, outer, upper, lower, etc.) may be used to facilitate discussion of the drawings and principles herein, but are not intended to be limiting. For example, certain terms may be used such as "inside," "outside,", "top," "down," "interior," "exterior," and the like. Such terms are used, where applicable, to provide some clarity of description when dealing with relative relationships, particularly with respect to the illustrated embodiments. Such terms are not, however, intended to imply absolute relationships, positions, and/or orientations. For example, with respect to an object, an "upper" part can become a "lower" part simply by turning the object over. Nevertheless, it is still the same part and the object remains the same. As used herein, "and/or" means "and" or "or," as well as "and" and or.

In the context of the present application, the terms "lower" and "upper" are used interchangeably with the term's "outlet" and "inlet", respectively. Thus, for example, the lower end of the valve is its outlet end and the upper end of the valve is its inlet end.

As used herein, with reference to the prosthetic medical device (e.g., heart valve), capsule, and the delivery apparatus, "proximal" refers to a position, direction, or portion of a component that is closer to the user and/or a handle of the delivery apparatus that is outside the patient, while "distal" refers to a position, direction, or portion of a component that is further away from the user and/or the handle of the delivery apparatus and closer to the implantation site. The terms "longitudinal" and "axial" refer to an axis extending in the proximal and distal directions, unless otherwise expressly defined. Further, the term "radial" refers to a direction that is arranged perpendicular to the axis and points along a radius from a center of an object (where the axis is positioned at the center, such as the longitudinal axis of the prosthetic heart valve).

In some of the illustrations previously discussed of the various embodiments of storage jar assemblies and the features thereof, only the frame, or only a part of the frame of prosthetic heart valves intended for use with the present invention are shown. This is done to assist with the clarity of the illustrations, and should be not be taken as limiting the scope of the invention.

Additional Examples of the Disclosed Technology

In view of the above-described implementations of the disclosed subject matter, this application discloses the additional examples enumerated below. It should be noted that one feature of an example in isolation or more than one feature of the example taken in combination and, optionally, in combination with one or more features of one or more further examples are further examples also falling within the disclosure of this application.

Example 1. A storage jar assembly, comprising: a jar having an open end and configured to receive a prosthetic heart valve; and a lid configured to cover the open end of the jar, the lid comprising a plurality of valve attachment features configured to be releasably attached to corresponding features of the prosthetic heart valve.

Example 2. The storage jar assembly of any example herein, particularly example 1, wherein the plurality of valve attachment features comprise notches formed on an inner surface of the lid, the notches configured to receive portions of a frame of the prosthetic heart valve.

Example 3. The storage jar assembly of any example herein, particularly example 2, wherein the inner surface of the lid comprises an annular lip, wherein the notches are formed on an inner peripheral edge of the annular lip.

Example 4. The storage jar assembly of any example herein, particularly example 2, wherein the inner surface of the lid comprises an annular lip, wherein the notches are formed on an outer peripheral edge of the annular lip.

Example 5. The storage jar assembly of any example herein, particularly examples 1-4 wherein the plurality of valve attachment features of the lid is configured to hold one end of the frame in a partially compressed state.

Example 6. The storage jar assembly of any of any example herein, particularly examples 1-5, wherein the plurality of valve attachment features is circumferentially spaced from each other along an imaginary circle centered around an axis extending through the lid.

Example 7. The storage jar assembly of any example herein, particularly example 6, wherein a diameter of the imaginary circle is selected to impart a desired holding force on the prosthetic heart valve.

Example 8. The storage jar assembly of any example herein, particularly examples 1-7, wherein the plurality of valve attachment features extends away from an interior surface of the lid.

Example 9. The storage jar assembly of any example herein, particularly examples 1-8, wherein the jar contains a hydrating fluid and a prosthetic heart valve.

Example 10. The storage jar assembly of any example herein, particularly example 9, wherein the hydrating fluid is glutaraldehyde.

Example 11. The storage jar assembly of any example herein, particularly examples 8-9, wherein the valve attachment features are configured to fully submerge the prosthetic heart valve in the hydrating fluid when the lid is attached to ajar.

Example 12. The storage jar assembly of any example herein, particularly examples 1-11, wherein the lid comprises a lid attachment mechanism configured to releasably attach to the jar near the open end.

Example 13. The storage jar assembly of any example herein, particularly example 12, wherein the lid attachment mechanism comprises a screw thread configured to engage a corresponding screw thread on the jar.

Example 14. The storage jar assembly of any example herein, particularly example 12, wherein the lid attachment mechanism comprises a ridge on the inside of the lid configured to releasably engage with a lip disposed on an exterior of the jar near the open end.

Example 15. A storage jar assembly, comprising: a jar having an open end and configured to receive a prosthetic heart valve; a lid configured to cover the open end of the jar; and a valve securement mechanism coupled to the lid and comprising a plurality of notches configured to be releasably attached to corresponding features of the prosthetic heart valve and hold one end of the prosthetic heart valve in at least a partially radially compressed state.

Example 16. The storage jar assembly of any example herein, particularly example 15, wherein the valve securement mechanism comprises an annular ring, wherein the notches are formed in the annular ring.

Example 17. The storage jar assembly of any example herein, particularly example 16, wherein the notches are formed in an inner peripheral edge of the annular ring.

Example 18. The storage jar assembly of any example herein, particularly example 16, wherein the notches are formed in an outer peripheral edge of the annular ring.

Example 19. The storage jar assembly of any example herein, particularly examples 16-18, wherein the annular ring is positioned below the lid.

Example 20. The storage jar assembly of any example herein, particularly example 19, wherein the valve securement mechanism comprises one or more struts interconnecting the annular ring to the lid.

Example 21. The storage jar assembly of any example herein, particularly examples 15-20, wherein the lid comprises a screw thread configured to engage a corresponding screw thread on the jar.

Example 22. The storage jar assembly of any example herein, particularly examples 15-20, wherein the lid comprises a ridge on the inside of the lid configured to releasably engage with a lip disposed on an exterior of the jar near the open end.

Example 23. The storage jar assembly of any example herein, particularly examples 15-20, wherein the jar contains a hydrating fluid and a prosthetic heart valve.

Example 24. The storage jar assembly of any example herein, particularly example 23, wherein the hydrating fluid is glutaraldehyde.

Example 25. The storage jar assembly of any example herein, particularly examples 23-24, wherein the valve securement mechanism is configured to fully submerge the prosthetic heart valve in the hydrating fluid when the lid is attached to ajar.

Example 26. A storage jar assembly, comprising a jar having an open end and configured to receive a prosthetic heart valve; a lid configured to cover the open end of the jar; and a valve holder comprising a base, a column, and plurality of valve retention members, wherein the column has a lower end portion coupled to the base, an upper end portion, and extends axially from the base; and the plurality of valve retention members extend upwardly from the base and are configured to contact an outer surface of the prosthetic heart valve.

Example 27. The storage jar assembly of any example herein, particularly example 26, wherein the plurality of valve retention members are disposed at circumferentially spaced locations on the base of the valve holder.

Example 28. The storage jar assembly of any example herein, particularly examples 26-27, wherein a position of the plurality of valve retention members is adjustable radially inwardly and outwardly relative to a central axis of the base.

Example 29. The storage jar assembly of any example herein, particularly examples 26-28, wherein the base comprises plurality of slots and each of the valve retention members comprises a projection that extends into a corresponding slot.

Example 30. The storage jar assembly of any example herein, particularly examples 26-28, wherein the base comprises plurality of projections and each of the valve retention members comprises a slot that receives a corresponding projection.

Example 31. The storage jar assembly of any example herein, particularly examples 26-30, wherein the plurality of valve retention members are configured to hold the prosthetic heart valve under a radial compressive strain.

Example 32. The storage jar assembly of any example herein, particularly example 31, wherein the radial compressive strain is less than 6%.

Example 33. The storage jar assembly of any example herein, particularly example 31, wherein the radial compressive strain is less than 3%.

Example 34. The storage jar assembly of any example herein, particularly example 31, wherein the radial compressive strain is less than 1%.

Example 35. The storage jar assembly of any example herein, particularly examples 26-34, wherein an inner diameter of the jar is less than an outer diameter of the prosthetic heart valve in its fully expanded state.

Example 36. The storage jar assembly of any example herein, particularly examples 26-35, wherein the upper end portion of the column comprises a handle to assist in withdrawing the valve holder from the jar.

Example 37. The storage jar assembly of any example herein, particularly examples 26-36, wherein the valve holder is configured to support the prosthetic heart valve within the jar for sterilization, shipping, and handling.

Example 38. The storage jar assembly of any example herein, particularly examples 26-37, wherein the base of the valve holder has an outer diameter that is less than 55 mm.

Example 39. The storage jar assembly of any example herein, particularly examples 26-38, wherein the lid comprises a lid attachment mechanism configured to be releasably attached to the jar near the open end.

Example 40. The storage jar assembly of any example herein, particularly example 39, wherein the lid attachment mechanism is a screw thread configured to engage a corresponding screw thread on the jar.

Example 41. The storage jar assembly of any example herein, particularly example 39, wherein the lid attachment mechanism comprises a ridge on the inside of the lid configured to releasably engage with a lip disposed on an exterior of the jar near the open end.

Example 42. The storage jar assembly of any example herein, particularly examples 26-41, wherein lid attached to the upper end portion of the column.

Example 43. The storage jar assembly of any example herein, particularly examples 26-41, wherein the lid is configured to be removably attached to the upper end portion of the column.

Example 44. The storage jar assembly of any example herein, particularly examples 26-43, wherein the jar contains a hydrating fluid and a prosthetic heart valve.

Example 45. The storage jar assembly of any example herein, particularly example 44, wherein the hydrating fluid is glutaraldehyde.

Example 46. A storage jar assembly, comprising a jar having an open end and configured to receive a prosthetic heart valve; a lid configured to cover the open end of the jar; and a valve holder configured to hold the prosthetic heart valve in a partially compressed state within the jar.

Example 47. The storage jar assembly of any example herein, particularly example 46, wherein the valve holder comprises a plurality of valve retention members.

Example 48. The storage jar assembly of any example herein, particularly example 47, wherein the position of the plurality of valve retention members is radially adjustable inwardly and outwardly relative to an outer circumference of the valve holder.

Example 49. The storage jar assembly of any example herein, particularly examples 46-48, wherein the valve holder comprises a base and a column having a lower end portion connected to the base and extending axially away from the base.

Example 50. The storage jar assembly of any example herein, particularly example 49, wherein the plurality of valve retention members is disposed along a surface of the base.

Example 51. The storage jar assembly of any example herein, particularly examples 49-50, wherein the base comprises a plurality of slots and each of the valve retention members comprises a projection that extends into a corresponding slot.

Example 52. The storage jar assembly of any example herein, particularly examples 49-50, wherein the base comprises one or more projections and each of the valve retention members comprises a slot that receives a corresponding projection.

Example 53. The storage jar assembly of any example herein, particularly examples 46-52, wherein the valve retention members are circumferentially spaced from each other.

Example 54. The storage jar assembly of any example herein, particularly examples 46-52, wherein the plurality of valve retention members are configured to hold the prosthetic heart valve under a radial compressive strain.

Example 55. The storage jar assembly of any example herein, particularly example 54, wherein the radial compressive strain is less than 6%.

Example 56. The storage jar assembly of any example herein, particularly example 54, wherein the radial compressive strain is less than 3%.

Example 57. The storage jar assembly of any example herein, particularly example 54, wherein the radial compressive strain is less than 1%.

Example 58. The storage jar assembly of any example herein, particularly examples 49-52, wherein the lid is configured to receive and secure an upper end portion of the column.

Example 59. The storage jar assembly of any example herein, particularly examples 46-58, wherein an inner diameter of the jar is less than an outer diameter of the prosthetic heart valve in its fully expanded state.

Example 60. The storage jar assembly of any example herein, particularly examples 46-59, wherein the lid comprises a lid attachment mechanism configured to releasably attach to the jar near the open end.

Example 61. The storage jar assembly of any example herein, particularly example 60, wherein the lid attachment mechanism is a screw thread configured to engage a corresponding screw thread on the jar.

Example 62. The storage jar assembly of any example herein, particularly example 60, wherein the lid attachment mechanism comprises a lip on the inside of the lid configured to releasably engage with a ridge disposed on the exterior of the jar near the open end.

Example 63. The storage jar assembly of any example herein, particularly examples 47-62, wherein the jar contains a hydrating fluid and a prosthetic heart valve.

Example 64. The storage jar assembly of any example herein, particularly example 63, wherein the hydrating fluid is glutaraldehyde.

Example 65. A lid, configured to cover an open end of a jar, comprising: an upper portion; a side wall depending from the upper portion; a valve attachment feature coupled to the lid and configured to releasably hold corresponding features of a prosthetic heart valve; and a valve release mechanism configured to detach the prosthetic heart valve from the valve attachment feature.

Example 66. The lid of any example herein, particularly example 65, wherein the valve release mechanism is a button.

Example 67. The lid of any example herein, particularly example 66, wherein the button is set in the upper portion of the lid and is configured to slide axially relative to the upper portion of the lid.

Example 68. The lid of example herein, particularly examples 65-67, wherein the valve attachment feature is a circular recession in the lid.

Example 69. The lid of any example herein, particularly examples 65-67, wherein the valve attachment feature is an annular recession formed in the lid.

Example 70. The lid of any example herein, particularly examples 65-67, wherein the valve attachment feature is a plurality of notches formed in the lid and circumferentially spaced from one another.

Example 71. The lid of any example herein, particularly examples 65-70, wherein the valve attachment feature is at least partially defined by the button.

Example 72. The lid of any example herein, particularly examples 65-71, wherein the prosthetic heart valve is retained in the valve attachment feature by an interference fit.

Example 73. The lid of any example herein, particularly examples 65-72, wherein the valve release mechanism is configured to press on the prosthetic heart valve and detach it from the valve attachment feature.

Example 74. The lid of any example herein, particularly examples 65-73, wherein the lid comprises a lid attachment mechanism configured to releasably attach to the jar near the open end.

Example 75. The lid of any example herein, particularly examples 65-74, wherein the lid attachment mechanism is a screw thread configured to engage a corresponding screw thread on the jar.

Example 76. The lid of any example herein, particularly examples 65-75, wherein the lid attachment mechanism comprises a lip on the inside of the lid configured to releasably engage with a ridge disposed on the exterior of the jar near the open end.

Example 77. A storage jar assembly, comprising: a jar having an open end and configured to receive a prosthetic heart valve; a lid, configured to cover an open end of the jar, comprising: an upper portion; a side wall depending from the upper portion; a valve attachment feature coupled to the lid and configured to releasably hold corresponding features of a prosthetic heart valve; and a valve release mechanism configured to detach the prosthetic heart valve from the valve attachment feature.

Example 78. The storage jar assembly of any example herein, particularly example 77, wherein the valve release mechanism is a button.

Example 79. The storage jar assembly any example herein, particularly example 78, wherein the button is set in the upper portion of the lid and is configured to slide axially relative to the upper portion of the lid.

Example 80. The storage jar assembly of any example herein, particularly examples 77-79, wherein the valve attachment feature is a circular recession in the lid.

Example 81. The storage jar assembly of any example herein, particularly examples 77-79, wherein the valve attachment feature is an annular recession formed in the lid.

Example 82. The storage jar assembly of any example herein, particularly examples 77-79, wherein the valve attachment feature is a plurality of notches formed in the lid and circumferentially spaced from one another.

Example 83. The storage jar assembly of any example herein, particularly examples 77-82, wherein the valve attachment feature is at least partially defined by the button.

Example 84. The storage jar assembly of any example herein, particularly examples 77-83, wherein the prosthetic heart valve is retained in the valve attachment feature by an interference fit.

Example 85. The storage jar assembly of any example herein, particularly examples 77-84, wherein the valve release mechanism is configured to press on the prosthetic heart valve and detach it from the valve attachment feature.

Example 86. The storage jar assembly of any example herein, particularly examples 77-85, wherein the lid comprises a lid attachment mechanism configured to releasably attach to the jar near the open end.

Example 87. The storage jar assembly of any example herein, particularly example 86, wherein the lid attachment mechanism is a screw thread configured to engage a corresponding screw thread on the jar.

Example 88. The storage jar assembly of any example herein, particularly example 87, wherein the lid attachment mechanism comprises a lip on the inside of the lid configured to releasably engage with a ridge disposed on the exterior of the jar near the open end.

Example 89. The storage jar assembly of any example herein, particularly examples 77-88, wherein the jar contains a hydrating fluid and a prosthetic heart valve.

Example 90. The storage jar assembly of any example herein, particularly example 89, wherein the hydrating fluid is glutaraldehyde.

Example 91. The storage jar assembly of any example herein, particularly example 90, wherein the valve release mechanism is configured to release the prosthetic heart valve into the hydrating fluid when used.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

I claim:

1. A storage jar assembly, comprising:
   a jar having an open end and configured to receive a prosthetic heart valve; and
   a lid configured to releasably attach to and cover the open end of the jar, the lid comprising an inner surface comprising an annular lip, and a plurality of valve attachment features configured to be releasably attached to corresponding features of the prosthetic heart valve, wherein the valve attachment features comprise a plurality of notches formed on an inner peripheral edge of the annular lip, the notches configured to receive portions of a frame of the prosthetic heart valve,
   wherein when the lid is attached to the open end of the jar, the lid is configured to retain a hydrating fluid inside the jar.

2. The storage jar assembly of claim 1, wherein the valve attachment features of the lid are configured to hold one end of the prosthetic heart valve in a partially compressed state.

3. The storage jar assembly of claim 1, wherein the valve attachment features extend away from an interior surface of the lid.

4. The storage jar assembly of claim 1, wherein the jar contains a hydrating fluid and a prosthetic heart valve.

5. The storage jar assembly of claim 4, wherein the valve attachment features are configured to at least partially submerge the prosthetic heart valve in the hydrating fluid when the lid is attached to the jar.

6. The storage jar assembly of claim 1, wherein the jar has an inner diameter and the inner diameter of the jar is smaller than an outer diameter of the prosthetic heart valve in a fully expanded state.

7. The storage jar assembly of claim 1, wherein the lid further comprises a valve release mechanism configured to detach the prosthetic heart valve from the valve attachment features.

8. The storage jar assembly of claim 1, wherein the lid further comprises a first helical thread and the jar comprises a second helical thread, and the first helical thread is configured to engage with the second helical thread for attaching the lid to the jar.

9. The storage jar assembly of claim 1, wherein the valve attachment features comprise an annular lip and one or more struts interconnecting the annular lip to the lid.

10. A storage jar assembly, comprising:
    a jar having an open end and configured to receive a prosthetic heart valve; and
    a lid configured to releasably attach to and cover the open end of the jar, the lid comprising an inner surface comprising an annular lip, and a plurality of valve attachment features configured to be releasably attached to corresponding features of the prosthetic heart valve, wherein the valve attachment features comprise a plurality of notches formed on an inner peripheral edge of the annular lip, the notches configured to receive portions of a frame of the prosthetic heart valve,
    wherein the valve attachment features of the lid are configured to hold one end of the prosthetic heart valve in a partially compressed state, wherein when the lid is attached to the open end of the jar, the lid is configured to retain a hydrating fluid inside the jar, and wherein the lid further comprises a first helical thread and the jar comprises a second helical thread, and the first helical thread is configured to engage with the second helical thread for attaching the lid to the jar.

11. The storage jar assembly of claim 10, wherein the valve attachment features are configured to at least partially submerge the prosthetic heart valve in the hydrating fluid when the lid is attached to the jar.

12. The storage jar assembly of claim 10, wherein the jar has an inner diameter and the inner diameter of the jar is smaller than an outer diameter of the prosthetic heart valve in a fully expanded state.

13. The storage jar assembly of claim 10, wherein the lid further comprises a valve release mechanism configured to detach the prosthetic heart valve from the valve attachment features.

14. The storage jar assembly of claim 10, wherein the lip and the notches are spaced from the inner surface of the lid to form a receiving space configured to receive corresponding features of the prosthetic heart valve.

15. A storage jar assembly, comprising:
a jar having an open end and configured to receive a prosthetic heart valve; and
a lid comprising an upper portion and an annular side wall that is connected to and extends downwardly from the upper portion, wherein the upper portion comprises a lower inner surface and a valve securement member projecting from the lower inner surface, wherein the lid is configured to releasably attach to and cover the open end of the jar, wherein the valve securement member comprises a plurality of valve attachment features are configured to be releasably attached to corresponding features of the prosthetic heart valve,
wherein the annular side wall extends downward past the plurality of valve attachment features and wherein when the lid is attached to the open end of the jar, the lid is configured to retain a hydrating fluid inside the jar.

16. The storage jar assembly of claim 15, wherein the valve securement member comprises an annular lip.

17. The storage jar assembly of claim 16, wherein the valve attachment features comprise a plurality of notches formed on an inner peripheral edge of the annular lip.

18. The storage jar assembly of claim 16, wherein the valve attachment features comprise a plurality of notches formed on an outer peripheral edge of the annular lip.

19. The storage jar assembly of claim 17, wherein the lip and the notches are spaced from the lower inner surface of the lid to form a receiving space configured to receive corresponding features of the prosthetic heart valve.

* * * * *